US011041929B2

United States Patent
Ji

(10) Patent No.: US 11,041,929 B2
(45) Date of Patent: Jun. 22, 2021

(54) SYSTEMS AND METHODS FOR SIGNAL SYNCHRONIZATION IN MRI DEVICE

(71) Applicant: SHANGHAI UNITED IMAGING HEALTHCARE CO., LTD., Shanghai (CN)

(72) Inventor: Ling Ji, Shanghai (CN)

(73) Assignee: SHANGHAI UNITED IMAGING HEALTHCARE CO., LTD., Shanghai (CN)

(*) Notice: Subject to any disclaimer, the term of this patent is extended or adjusted under 35 U.S.C. 154(b) by 113 days.

(21) Appl. No.: 16/458,391

(22) Filed: Jul. 1, 2019

(65) Prior Publication Data

US 2020/0057129 A1 Feb. 20, 2020

(30) Foreign Application Priority Data

Aug. 14, 2018 (CN) .......................... 201810924045.6
Nov. 13, 2018 (CN) .......................... 201811345082.8
Nov. 13, 2018 (CN) .......................... 201821871922.X

(51) Int. Cl.
*G01R 33/567* (2006.01)
*G01R 33/36* (2006.01)
*G01R 33/341* (2006.01)
*A61B 5/055* (2006.01)

(52) U.S. Cl.
CPC ......... *G01R 33/567* (2013.01); *G01R 33/341* (2013.01); *G01R 33/3671* (2013.01); *A61B 5/055* (2013.01); *G01R 33/3621* (2013.01)

(58) Field of Classification Search
CPC .............. G01R 33/341; G01R 33/3671; G01R 33/3621; G01R 33/567; A61B 5/055
See application file for complete search history.

(56) References Cited

U.S. PATENT DOCUMENTS

| | | | |
|---|---|---|---|
| 5,245,288 A | 9/1993 | Leussler | |
| 7,443,165 B2 | 10/2008 | Varjo | |
| 7,834,628 B2 | 11/2010 | Biber et al. | |
| 8,598,874 B2 | 12/2013 | Saes et al. | |
| 8,643,362 B2 | 2/2014 | Sekiguchi et al. | |
| 9,091,740 B2 | 7/2015 | Kwon et al. | |
| 9,519,038 B2 | 12/2016 | Okamoto et al. | |
| 9,658,302 B2 | 5/2017 | Kwon et al. | |
| 10,175,313 B2 | 1/2019 | Okamoto | |
| 2011/0109316 A1* | 5/2011 | Akita | G01R 33/3621 324/322 |
| 2014/0107467 A1* | 4/2014 | Felmlee | A61B 5/0035 600/411 |

(Continued)

*Primary Examiner* — Gregory H Curran
(74) *Attorney, Agent, or Firm* — Metis IP LLC

(57) ABSTRACT

Systems and methods for MR signal synchronization may be provided. The method may include determining a time difference in a local clock generator at a coil side assembly compared to a system clock generator at a system side assembly. The method may include maintaining a constant phase difference between clock signals generated by the local clock generator and by the system clock generator by correcting the local clock generator based on the time difference. The method may include acquiring MR echo signals by scanning at least a part of a subject in response to the clock signal generated by the corrected local clock generator. The method may further include digitizing the MR echo signal at the coil side assembly.

14 Claims, 16 Drawing Sheets

(56) References Cited

U.S. PATENT DOCUMENTS

2016/0069969 A1* 3/2016 Tomiha .............. G01R 33/3692
324/322
2018/0106875 A1 4/2018 Duensing et al.
2019/0094318 A1 3/2019 Okamoto

* cited by examiner

SYSTEMS AND METHODS FOR SIGNAL SYNCHRONIZATION IN MRI DEVICE

CROSS-REFERENCE OF RELATED APPLICATIONS

This application claims priority of Chinese Patent Application No. 201810924045.6, filed on Aug. 14, 2018, Chinese Patent Application No. 201821871922.X, filed on Nov. 13, 2018, and Chinese Patent Application No. 201811345082.8, filed on Nov. 13, 2018, the contents of which are hereby incorporated by reference.

TECHNICAL FIELD

The present disclosure generally relates to an imaging device, and more particularly, relates to a magnetic resonance imaging (MRI) device and signal synchronization in the MRI device.

BACKGROUND

Magnetic resonance imaging (MRI) is a medical imaging technique used the principle of nuclear magnetic resonance. In MRI, radio frequency (RF) wave may be emitted and directed at nuclei, for example, protons, in a strong external magnetic field. The energy of the RF wave may be attenuated when going through a subject (or at least one portion of the subject). The protons may be excited and then relaxed. RF signals (e.g., MR signals) may be generated accordingly. The generated RF signals may be detected by one or more RF receiving coils. A computing device (e.g., a computer) coupled with the MRI device may form an MR image by processing the RF signals. For MRI, MR signals may need to be acquired synchronously by the one or more RF receiving coils. The MR signals may be sent to a system side of the MRI device (e.g., the computing device at the system side). However, in some cases, the acquisition of MR signals by at least part of the RF receiving coils may lack synchronism, which may cause phase errors and in turn result in image artifacts. Therefore, it is desirable to develop systems and methods for MR signal synchronization in order to reduce the image artifact and improve the image quality of the MR image.

SUMMARY

In a first aspect of the present disclosure, a method for magnetic resonance (MR) signal synchronization between a coil side assembly and a system side assembly of a magnetic resonance imaging (MRI) device is provided. The method may include one or more of the following operations. At least one processor may be configured to determine a time difference in a local clock generator at the coil side assembly compared to a system clock generator at the system side assembly. The at least one processor may be configured to maintain a constant phase difference between clock signals generated by the local clock generator and by the system clock generator by correcting the local clock generator based on the time difference. The at least one processor may be configured to acquire MR echo signals by scanning at least a part of a subject in response to the clock signal generated by the corrected local clock generator. The at least one processor may be configured to digitize the MR echo signal at the coil side assembly.

In some embodiments, the at least one processor may be configured to wirelessly send, via a signal transmitter system, the digitized MR echo signal from the coil side assembly to the system side assembly.

In some embodiments, the at least one processor may be configured to determine a time delay in the local clock generator compared to the system clock generator, and determine the time difference based on the time delay.

In some embodiments, the at least one processor may be configured to send, at the coil side assembly, a first Sync message to the system side assembly, the first Sync message including a first timestamp recording when the first Sync message is sent by the coil side assembly. The at least one processor may be configured to receive, at the coil side assembly, a second Sync message from the system side assembly, and registering a fourth timestamp recording when the second Sync message is received by the coil side assembly, the second Sync message including the first timestamp, a second timestamp recording when the first Sync message is received by the system side assembly, and a third timestamp recording when the second Sync message is sent by the system side assembly. The at least one processor may be configured to determine the time delay based on the first timestamp, the second timestamp, the third timestamp, and the fourth timestamp.

In some embodiments, the at least one processor may be configured to receive, at the coil side assembly, a first Sync message from the system side assembly, and register a first timestamp recording when the first Sync message is received by the coil side assembly. The at least one processor may be configured to receive, at the coil side assembly, a second Sync message from the system side assembly, the second Sync message including a second timestamp recording when the first Sync message is sent by the system side assembly. The at least one processor may be configured to send, at the coil side assembly, a third Sync message to the system side assembly, and register a third timestamp recording when the third Sync message is sent by the coil side assembly. The at least one processor may be configured to receive, at the coil side assembly, a fourth Sync message from the system side assembly, the fourth Sync message including a fourth timestamp recording when the third Sync message is received by the system side assembly. The at least one processor may be configured to determine the time delay based on the first timestamp, the second timestamp, the third timestamp, and the fourth timestamp.

In some embodiments, the at least one processor may be configured to amplify the MR echo signal. The at least one processor may be configured to filter the amplified MR echo signal. The at least one processor may be configured to digitize the filtered MR echo signal by performing analog to digital signal conversion.

In some embodiments, the at least one processor may be configured to generate a K space dataset, at the system side assembly, based on the MR echo signals. The at least one processor may be configured to reconstruct, at the system coil assembly, an MR image based on the K space dataset.

In some embodiments, the coil side assembly may comprise a plurality of radio frequency (RF) receiving coils. For each of the plurality of radio frequency (RF) receiving coils, the at least one processor may be configured to send, via a signal transmitter system, wirelessly a request for communicating with the system side assembly to the system side assembly, the request including a first timestamp recording when the request is sent by the RF receiving coil. The at least one processor may be configured to receive, via the signal transmitter system, wirelessly a permission from the system side assembly to communicate with the system side assembly, the permission including the first timestamp, a second timestamp recording when the request is received by the system side assembly, a third timestamp recording when the response is sent by the system side assembly. The at least one processor may be configured to register a fourth timestamp recording when the permission is received by the RF receiving coil. The at least one processor may be configured to determine the time difference in the RF receiving coil compared to the system side assembly based on the first timestamp, the second timestamp, the third timestamp, and the fourth timestamp.

In some embodiments, the request may further include a coil characteristic of the RF receiving coil. The at least one processor may be configured to assign, at the system side assembly and based on the coil characteristic, a signal channel for communication between the RF receiving coil and the system side assembly in response to the request. The at least one processor may be configured to send via the signal channel, the permission to the coil side assembly.

In some embodiments, the at least one processor may be configured to assign the signal channel for the RF receiving coil using a Frequency Division Multiple Access (FDMA) technique or a Code Division Multiple Access (CDMA) technique.

According to another aspect of the present disclosure, a system is provided. The system may include a storage device including a set of instructions, and at least one processor in communication with the storage device. When executing the set of instructions, the at least one processor may be configured to determine a time difference in a local clock generator at the coil side assembly compared to a system clock generator at the system side assembly. The at least one processor may be configured to maintain a constant phase difference between clock signals generated by the local clock generator and by the system clock generator by correcting the local clock generator based on the time difference. The at least one processor may be configured to acquire MR echo signals by scanning at least a part of a subject in response to the clock signal generated by the corrected local clock generator. The at least one processor may be configured to digitize the MR echo signal at the coil side assembly.

According to another aspect of the present disclosure, a system is provided. The system may include a storage device including a set of instructions, and at least one processor in communication with the storage device. When executing the set of instructions, for each of a plurality of radio frequency (RF) receiving coils disposed in the coil side assembly, the at least one processor may be configured to send, via a signal transmitter system, wirelessly a request for communicating with the system side assembly to the system side assembly, the request including a first timestamp recording when the request is sent by the RF receiving coil. The at least one processor may be configured to receive, via the signal transmitter system, wirelessly a permission from the system side assembly to communicate with the system side assembly, the permission including the first timestamp, a second timestamp recording when the request is received by the system side assembly, a third timestamp recording when the response is sent by the system side assembly. The at least one processor may be configured to register a fourth timestamp recording when the permission is received by the RF receiving coil. The at least one processor may be configured to determine a time difference in the RF receiving coil compared to the system side assembly based on the first timestamp, the second timestamp, the third timestamp, and the fourth timestamp. The at least one processor may be configured to maintain a constant phase difference between clock signals generated by the local clock generator and a system clock generator by correcting, based on the time difference, a local clock generator of the RF receiving coil.

Additional features will be set forth in part in the description which follows, and in part will become apparent to those skilled in the art upon examination of the following and the accompanying drawings or may be learned by production or operation of the examples. The features of the present disclosure may be realized and attained by practice or use of various aspects of the methodologies, instrumentalities, and combinations set forth in the detailed examples discussed below.

BRIEF DESCRIPTION OF THE DRAWINGS

The present disclosure is further described in terms of exemplary embodiments. These exemplary embodiments are described in detail with reference to the drawings. These embodiments are non-limiting exemplary embodiments, in which like reference numerals represent similar structures throughout the several views of the drawings, and wherein.

DETAILED DESCRIPTION

Figure 1A:
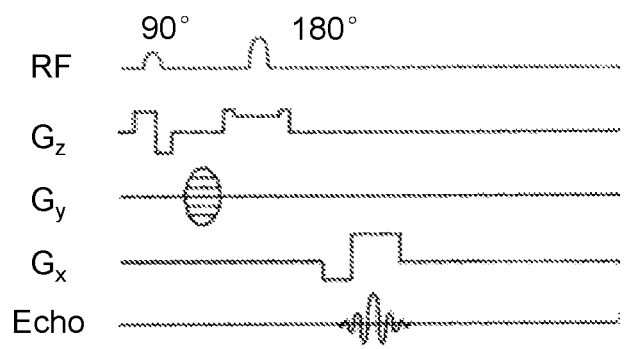
FIG. 1A and FIG. 1B are schematic diagrams illustrating exemplary spin-echo (SE) sequences according to some embodiments of the present disclosure.

The following description is presented to enable any person skilled in the art to make and use the present disclosure, and is provided in the context of a particular application and its requirements. Various modifications to the disclosed embodiments will be readily apparent to those skilled in the art, and the general principles defined herein may be applied to other embodiments and applications without departing from the spirit and scope of the present disclosure. Thus, the present disclosure is not limited to the embodiments shown, but is to be accorded the widest scope consistent with the claims.

The terminology used herein is for the purpose of describing particular exemplary embodiments only and is not intended to be limiting. As used herein, the singular forms "a," "an," and "the" may be intended to include the plural forms as well, unless the context clearly indicates otherwise. It will be further understood that the terms "comprise," "comprises," and/or "comprising," "include," "includes," and/or "including", when used in this specification, specify the presence of stated features, integers, steps, operations, elements, and/or components, but do not preclude the presence or addition of one or more other features, integers, steps, operations, elements, components, and/or groups thereof.

It will be understood that the term "system," "engine," "unit," and/or "module" used herein are one method to distinguish different components, elements, parts, section or assembly of different level in ascending order. However, the terms may be displaced by another expression if they achieve the same purpose.

Generally, the word "module" or "unit" as used herein, refers to logic embodied in hardware or firmware, or to a collection of software instructions. A module or a unit described herein may be implemented as software and/or hardware and may be stored in any type of non-transitory computer-readable medium or another storage device. In some embodiments, a software module/unit may be compiled and linked into an executable program. It will be appreciated that software modules can be callable from other modules/units or themselves, and/or may be invoked in response to detected events or interrupts. Software modules/units configured for execution on computing devices may be provided on a computer-readable medium, such as a compact disc, a digital video disc, a flash drive, a magnetic disc, or any other tangible medium, or as a digital download (and can be originally stored in a compressed or installable format that needs installation, decompression, or decryption prior to execution). Such software code may be stored, partially or fully, on a storage device of the executing computing device, for execution by the computing device. Software instructions may be embedded in firmware, such as an EPROM. It will be further appreciated that hardware modules/units may be included in connected logic components, such as gates and flip-flops, and/or can be included of programmable units, such as programmable gate arrays or processors. The modules/units or computing device functionality described herein may be implemented as software modules/units but may be represented in hardware or firmware. In general, the modules/units described herein refer to logical modules/units that may be combined with other modules/units or divided into sub-modules/sub-units despite their physical organization or storage. The description may apply to a system, an engine, or a portion thereof.

It will be understood that when a unit, engine or module is referred to as being "on," "connected to," or "coupled to," another unit, engine, or module, it may be directly on, connected or coupled to, or communicate with the other unit, engine, or module, or an intervening unit, engine, or module may be present, unless the context clearly indicates otherwise. As used herein, the term "and/or" includes any and all combinations of one or more of the associated listed items.

These and other features, and characteristics of the present disclosure, as well as the methods of operation and functions of the related elements of structure and the combination of parts and economies of manufacture, may become more apparent upon consideration of the following description with reference to the accompanying drawings, all of which form a part of the present disclosure. It is to be expressly understood, however, that the drawings are for the purpose of illustration and description only and are not intended to limit the scope of the present disclosure. It is understood that the drawings are not to scale.

Provided herein are systems and components for medical imaging and/or medical treatment. In some embodiments, the medical imaging system may include a single modality imaging system and/or a multi-modality imaging system. The single modality imaging system may include, for example, a magnetic resonance imaging (MRI) system. Exemplary magnetic resonance imaging (MRI) system may include a superconducting magnetic resonance imaging device, a non-superconducting magnetic resonance imaging system, etc. The multi-modality imaging system may include, for example, a computed tomography-magnetic resonance imaging (MR I-CT) system, a positron emission tomography-magnetic resonance imaging (PET-MRI) system, a single photon emission computed tomography-magnetic resonance imaging (SPECT-MRI) system, a digital subtraction angiography-magnetic resonance imaging (DSA-MRI) system, etc.

For illustration purposes, the disclosure describes systems and methods for MRI medical applications (e.g., MRI imaging, MRI guided radiotherapy treatment, etc.). It should be noted that the MRI system and/or the MRI device described below is merely provided for illustration purposes, and not intended to limit the scope of the present disclosure.

Magnetic resonance imaging (MRI) is a type of tomography imaging, which uses magnetic resonance phenomena generated by the nucleus in the human body to imaging. In some cases, in contrast with computed tomography (CT), MRI may provide a high image resolution and a good image contrast for soft tissues patients. MRI may be well suited to medical examinations for a patient's brain, muscle, heart, and tumor relative to other medical imaging techniques. MRI does not involve ionizing radiation, and has few side effects on the patients. The MRI may reduce or avoid the bone artifacts. In some embodiments, in the MRI, a variety of scan parameters may be selected. It is convenient to provide diagnostic means for examining some lesions in organs of a whole body. For example, the MRI may provide an earlier diagnostic basis for a tumor lesion. The MRI may rely on the Hydrogen nuclei. More than 60% of the human body's weight is water, whose main element is hydrogen nuclei. The MRI may be sensitive to tissues with high water ratios. For example, when somebody has a lesion, a proportion of the water in the human body may change accordingly. The MRI may assist to determine a lesion reason by judging changes of the water in the MR image.

In an MRI device or MRI system, a magnetic body (e.g., a superconducting magnet) may be used to generate a uniform static magnetic field. In the uniform static magnetic field, one or more RF transmitting coils may be used to emit RF waves in order to excite Hydrogen nucleus to produce a spin precession for generating MR signals. One or more gradient coils may be used to encode the spatial information of MR signals. One or more RF receiving coils may be used to receive the MR signals. The MR signals may be converted into digital signals through a receiving link. A computing device may reconstruct an MR image based on the digitalized MR signals.

Figure 1B:
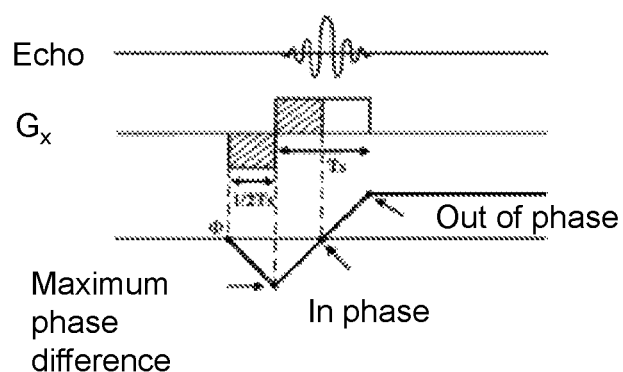

The MRI device and/or the MRI system may control magnetic field gradients in an X direction, a Y direction, and/or a Z direction (e.g., Gx, Gy, Gz) and RF pluses. When the magnetic field gradients and the RF pluses satisfy time sequence requirements, MR echo signals may be generated. However, in some cases, at least part of the RF receiving coils may not acquire MR echo signals synchronously, which may cause phase errors resulting in image artifacts in the phase encoding direction (e.g., Gy direction). Taking spin-echo (SE) sequences as an example, FIG. 1A and FIG. 1B illustrate SE sequences in one TR (i.e., repetition time that equals to a time interval between two adjacent 90° RF pulses). As shown in FIG. 1A, in one TR, the RF pulse sequence may include a 90° RF pulse, and at least one 180° RF pulse. An MR echo signal may be generated under the gradient sequences (Gx, Gy, Gz) and the RF pluses. FIG. 1B illustrates a relationship between the MR echo signal and a readout gradient (e.g., Gx). To generate an accurate MR echo signal, a negative Gx gradient may be applied, and last for a half of an acquisition time (e.g., ½ Ts). The maximum phase difference of protons spin may be generated. In the case, protons spin may be out of phase. Then a positive Gx gradient may be applied, proton spins may become in phase at the center of echo signal. It should be noted that the center of each echo signal in each of a plurality of TRs may be aligned in K space so as to reduce image artifact in a reconstructed MR image. Otherwise, the image artifact may be generated. Various embodiments of the present disclosure relate to systems and methods for MR echo signal synchronization that may reduce the image artifact and improve the image quality of the MR image.

Figure 2A:
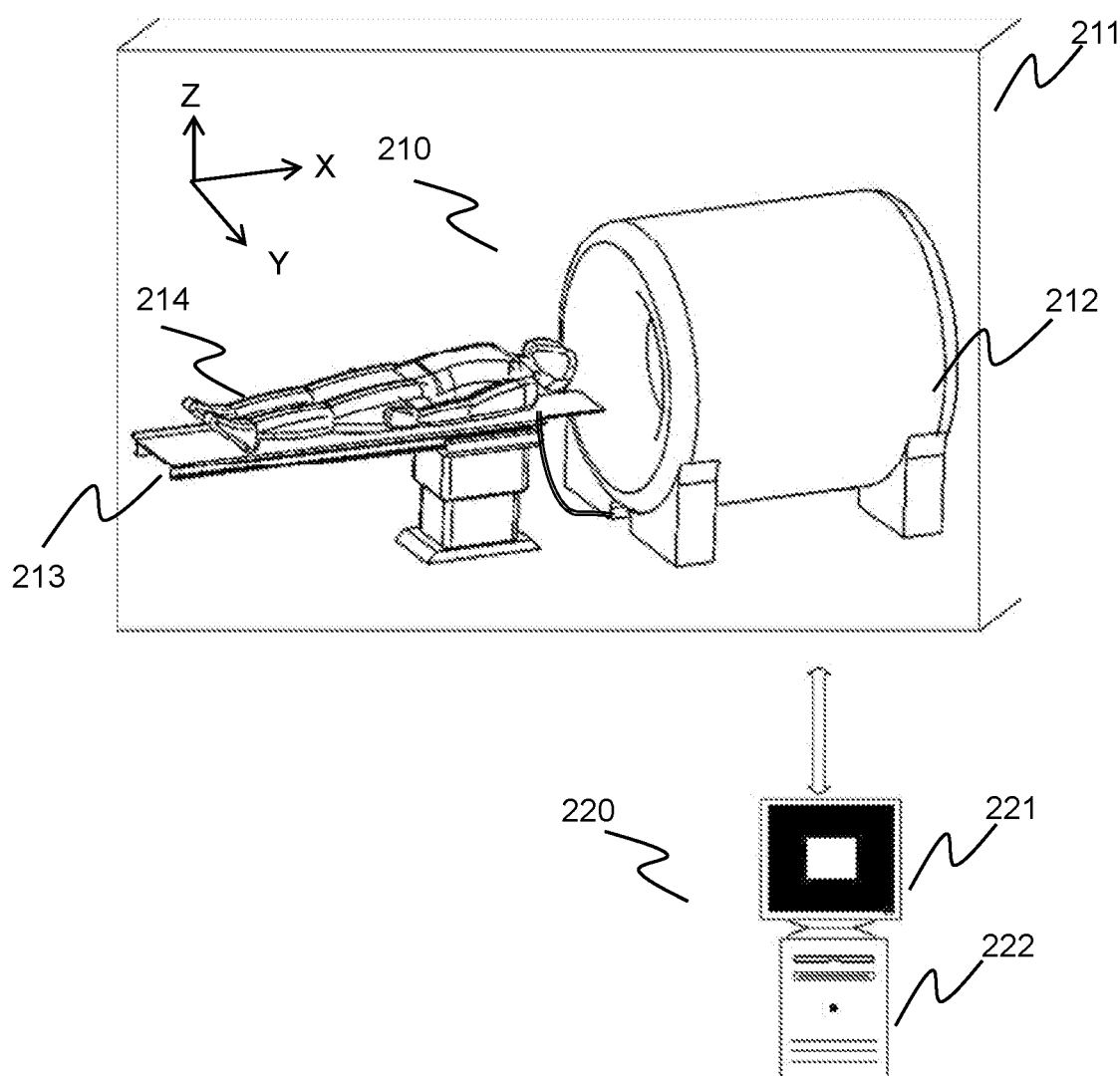
FIG. 2A is a schematic diagram illustrating an exemplary imaging system according to some embodiments of the present disclosure.

FIG. 2A is a schematic diagram illustrating an exemplary imaging system according to some embodiments of the present disclosure. Imaging system 200 may include a magnetic resonance imaging (MRI) system, a computed tomography-magnetic resonance imaging (MRI-CT) system, a positron emission tomography-magnetic resonance imaging (PET-MRI) system, a single photon emission computed tomography-magnetic resonance imaging (SPECT-MRI) system, a digital subtraction angiography-magnetic resonance imaging (DSA-MRI) system, and so on. As shown in FIG. 2A, the imaging system 200 may include a scanning system 210 for scanning a subject and a console 220 for operating or controlling the scanning system 210 via a network (e.g., a wireless network and/or a wired network). Taking the MRI system as an example, as shown in FIG. 2A, the scanning system 210 may be located within a scan room 211, and the console 220 may be located outside of the scan room 211. The console 220 may remotely control the scanning system 210. In some embodiments, the scanning system 210 and the console 220 may be located within the same scan room 211. In some embodiments, the scanning system 210 and the console 220 may be integrated into a single MRI device. The scanning system 210 may include a scanner 212, a scanning bed 213 electrically and/or mechanically connected to the scanner 212. The scanner 212 may be configured to scan at least one portion of a subject 214. The subject may be biological or non-biological. Merely by way of example, the subject may include a patient, a man-made object, etc. The subject may also include a specific portion, organ, and/or tissue of the patient. For example, the subject may include a head, a brain, a neck, a body, a shoulder, an arm, a thorax, a cardiac, a stomach, blood vessels, soft tissues, a knee, feet, or the like, or any combination thereof. The scanning bed 213 may be movable to support the subject 214 in response to control instructions from the scanner 212 or the console 220. In some embodiments, the scanner 212 may include a cavity structure for accommodating at least part of the subject 214 and the scanning bed 213. The cavity structure may be enclosed with one or more components, such as a superconducting magnet, a gradient coil, and so on. The one or more components of the scanner 212 may be described in connection with FIG. 2B.

As shown in FIG. 2A, the console 220 may include an input/output (I/O) device 221, a controller 222. In some embodiments, a user (e.g., a doctor or a technician) may control the position of the scanning bed 213 relative to the scanner 212 through the console 220, for example, having the scanning bed 213 moved to a specified position in response to one or more instructions from the console 220. The user may preset or adjust, through the I/O device 221, the specified location coordinates (e.g., the X axis, the Y axis, the Z axis) suitable to scan the subject. In some embodiments, the size of the cavity structure of the scanner 212 may be greater than or equal to the size of the scanning bed 213 in the width direction (e.g., in the Y direction). As used herein, the X direction, the Y direction, and the Z direction may represent an X axis, a Y axis, and a Z axis in a coordinate system. Merely by way of example, the X axis and the Z axis may be in a vertical horizontal plane, the X axis and the Y axis may be in a horizontal plane, the X axis may be along the axis of the magnetic body of the scanner 212.

The I/O device 221 may include a man-machine interactive device, such as a mouse, a keyboard, a joystick, a trackball, a display, etc. In some embodiments, the display may present subject information (e.g., height, weight, age, etc.), one or more scan parameters (e.g., a scan region, exposure parameters, sampling time, etc.), an operation status of the scanner (e.g., working hours, fault or not, etc.), or the like, or any combination thereof. Exemplary displays may include a cathode ray tube (CRT) display, a liquid crystal display (LCD), an organic light emitting display (OLED), a plasma display, an active matrix/organic light emitting diode (AMOLED) display, or the like, or any combination thereof.

The controller 222 may include a processing device (e.g., a processor) for receiving and processing data or information from one or more components of the imaging system 200 (e.g., the scanner 212 of the scanning system 210, the I/O device 221 of the console 220). For example, the controller 222 may receive one or more scan instructions via the I/O device 221, and direct the scanner 212 to scan the subject according to the one or more scan instructions. As another example, the controller 222 may receive MR echo signals from the scanner 212, and reconstruct an MR image by processing the MR echo signals.

In some embodiments, the controller 222 may include one or more of a main magnetic controller, a gradient coil controller, an RF controller, a clock generator controller, and an image processing controller. For example, the main magnetic controller may control the operation of the main magnetic body (e.g., a main magnetic body 212-1 illustrated in FIG. 2B). The gradient coil controller may control the operation of the gradient coil (e.g., the gradient coil 212-2 illustrated in FIG. 2B). The RF controller may control the operation of the one or more RF coils (e.g., a transmitting coil 212-3 and a receiving coil 212-4 illustrated in FIG. 2B). The clock generator controller may control the operation of the system clock generator or the local clock generator (not shown in the FIG. 2A and FIG. 2B). The image processing controller may perform the operation of imaging processing, for example, reconstructing an MR image by processing MR signals.

Merely for illustration, the processing device included in the controller 222 may include one or more hardware processors, such as a microcontroller, a microprocessor, a reduced instruction set computer (RISC), an application specific integrated circuits (ASICs), an application-specific instruction-set processor (ASIP), a central processing unit (CPU), a graphics processing unit (GPU), a physics processing unit (PPU), a microcontroller unit, a digital signal processor (DSP), a field programmable gate array (FPGA), an advanced RISC machine (ARM), a programmable logic device (PLD), any circuit or processor capable of executing one or more functions, or the like, or any combinations thereof.

It should be noted that the controller 222 in the present disclosure may also include one or more processors. Thus operations and/or method steps that are performed by one processor as described in the present disclosure may also be jointly or separately performed by the multiple processors. For example, if in the present disclosure the processor of the controller 222 executes both process A and process B, it should be understood that process A and process B may also be performed by two or more different processors jointly or separately in the controller 222 (e.g., a first processor executes process A and a second processor executes process B, or the first and second processors jointly execute processes A and B).

In some embodiments, one or more components of the console 220 (e.g., the I/O device 221 or the controller 222) may communicate with the one or more components of the scanning system 210 (e.g., the scanning bed 213, or the scanner 212) through a network (not shown in FIG. 2A). The network may facilitate the exchange of information and/or data. In some embodiments, the network may be any type of wired or wireless network, or combination thereof. The network may be and/or include a public network (e.g., the Internet), a private network (e.g., a local area network (LAN), a wide area network (WAN)), etc.), a wired network (e.g., an Ethernet network), a wireless network (e.g., an 802.11 network, a Wi-Fi network), a cellular network (e.g., a Long Term Evolution (LTE) network), a frame relay network, a virtual private network ("VPN"), a satellite network, a telephone network, routers, hubs, switches, server computers, and/or any combination thereof. Merely by way of example, the network may include a cable network, a wireline network, an optical fiber network, a telecommunications network, an intranet, an Internet, a local area network (LAN), a wide area network (WAN), a wireless local area network (WLAN), a metropolitan area network (MAN), a wide area network (WAN), a public telephone switched network (PSTN), a Bluetooth™ network, a Zig-Bee™ network, a near field communication (NFC) network, or the like, or any combination thereof.

In some embodiments, the console 220 may include one or more storage devices for storing data or information from one or more components of the imaging system 200 (e.g., the scanner 212 of the scanning system 210, the I/O device 221 or the controller 222 of the console 220). For example, the one or more storage devices may store scan parameters (e.g., scan protocols) input by the user. As another example, the one or more storage devices may store signals acquired by the scanner 212, and/or data or information generated during the period of processing the signals. In some embodiments, the one or more storage devices may store data and/or instructions that the controller 222 may execute or use to perform exemplary methods described in the present disclosure. For example, the one or more storage devices may store data and/or instructions that the processing device may execute or use to transmit MR echo signals to the console 220 synchronously, and/or reconstruct an MR image based on the MR echo signals. As another example, the one or more storage devices may store one or more instructions for moving the scanning bed 213 to the field of view (FOV) region from I/O device 221. As a further example, the one or more storage devices may store one or more instructions for scanning a target object. In response to the one or more instructions, the scanner 212 may perform one or more scans for the target object in the FOV region. The target object may include and/or be a subject, at least one part of the subject, such as, a head, a chest, a lung, a pleura, a mediastinum, an abdomen, a large intestine, a small intestine, a bladder, a gallbladder, triple burner, a pelvis, a bone, limbs, a skeleton, blood vessels, or the like, or any combination thereof.

In some embodiments, the storage device may include a mass storage device, a removable storage device, a volatile read-and-write memory, a read-only memory (ROM), or the like, or any combination thereof. Exemplary mass storage devices may include a magnetic disk, an optical disk, a solid-state drive, etc. Exemplary removable storage devices may include a flash drive, a floppy disk, an optical disk, a memory card, a zip disk, a magnetic tape, etc. Exemplary volatile read-and-write memory may include a random-access memory (RAM). Exemplary RAM may include a dynamic RAM (DRAM), a double date rate synchronous dynamic RAM (DDR SDRAM), a static RAM (SRAM), a thyristor RAM (T-RAM), and a zero-capacitor RAM (Z-RAM), etc. Exemplary ROM may include a mask ROM (MROM), a programmable ROM (PROM), an erasable programmable ROM (PEROM), an electrically erasable programmable ROM (EEPROM), a compact disk ROM (CD-ROM), and a digital versatile disk ROM, etc. In some embodiments, the storage device may be implemented on a cloud platform. Merely by way of example, the cloud platform may include a private cloud, a public cloud, a hybrid cloud, a community cloud, a distributed cloud, an inter-cloud, a multi-cloud, or the like, or any combination thereof.

Merely for illustration, the scanning system 210 and the console 220 may separate from each other described in the present disclosure. However, it should be noted that the scanning system 210 and the console 220 may be integrated into a single system. In some embodiments, the console 220 may be implemented on a cloud platform. For example, the cloud platform may include a private cloud, a public cloud, a hybrid cloud, a community cloud, a distributed cloud, an inter-cloud, a multi-cloud, or the like, or any combination thereof. For those skilled in the art, the console 220 may include an exemplary computing device having hardware and/or software components. The computing device may be a computer with user interface elements may be used to implement a personal computer (PC) or another type of work station or terminal device (e.g., a mobile device).

Figure 2B:
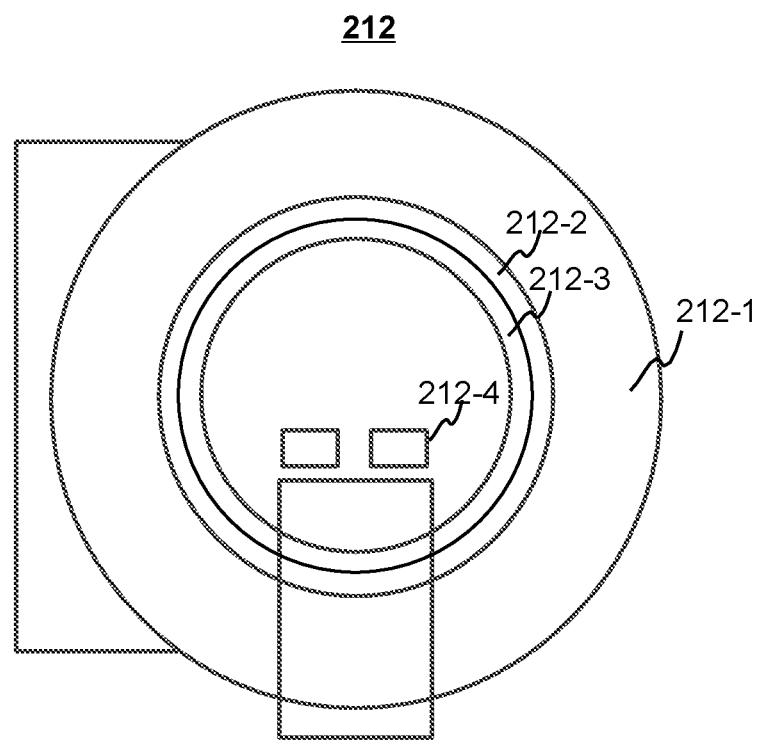
FIG. 2B is a schematic diagram illustrating exemplary portions of an MRI scanner according to some embodiments of the present disclosure.

FIG. 2B illustrates exemplary portions of the scanner 212 of the MRI system according to some embodiments of the present disclosure. In some embodiments, the scanner 212 may include a main magnetic body 212-1, a gradient coil 212-2, and one or more RF coils (e.g., a transmitting coil 212-3 and a receiving coil 212-4). In some embodiments, the main magnet body 212-1, the gradient coil 212-2, and the body coil 212-3 may be arranged in a gantry of the scanner 212.

In some embodiments, the main magnetic body 212-1 having an annular cylindrical structure may, along the axial direction of the main magnetic body 212-1, form a cavity for accommodating at least part of the subject 214 and the scanning bed 213. The gradient coil 212-2 may be disposed in the cavity. The main magnetic body 212-1 may be of various types including, for example, a permanent magnet, a superconducting electromagnet, a resistive electromagnet, etc. For example, the main magnetic body 212-1 may be a superconducting magnet including a coil rack (not shown in FIG. 2B), a plurality of superconducting coils wrapped on the coil rack, and a casing (not shown in FIG. 2B) enclosed the coil rack. The main magnetic body 212-1 may have a cylindrical shape, and its central axis may extend along the cavity. The main magnetic body 212-1 may generate a static magnetic field during the scanning of the at least one portion of the subject. The static magnetic field may also be referred to as a main magnetic field.

In some embodiments, the gradient coil 212-2 may at least include three sub-gradient coil sets, that is, Gx gradient coils, Gy gradient coils, and Gz gradient coils, respectively. The gradient direction generated by each of the three sub-gradient coil sets may be orthogonal to each other in space. In some embodiments, Gx gradient coils, Gy gradient coils, and Gz gradient coils may provide magnetic field gradients to the main magnetic field in an X direction, a Y direction, and a Z direction, respectively (see FIG. 2A). As used herein, the X direction, the Y direction, and the Z direction may represent an X axis, a Y axis, and a Z axis in a spatial coordinate system. The coordinate system may be designated as the reference coordinates applied to the scanning bed 213, the magnetic field gradient generated by the gradient coil 212-2, and/or the gradient direction of three logical axes in a pulse sequence. In some embodiments, the three sub-gradient coil sets may be operated separately, or any sub-gradient coil sets may be operated simultaneously, or all the sub-gradient coil sets may be operated simultaneously. The magnetic field gradient in any direction may be provided according to corresponding gradient pulse sequence. In some embodiments, the three sub-gradient coil sets of the gradient coil 212-2 may form as a whole body, for example, through an injection-molded with resin materials or other insulating materials, having the cylindrical structure, so as that it may be adapted to be disposed in the cavity. In some embodiments, the casing of the gradient coil 212-2 may be formed by insulating materials, which is sealed and airtight.

In some embodiments, the RF coil may include a body coil and/or a local coil. For example, the body coil and/or the local coil may include a birdcage coil, a solenoid coil, a saddle coil, a Helmholtz coil, a phased array coil, a loop coil, or the like, or any combination thereof. In some embodiments, the body coil and/or the local coil may be configured to emit excitation signals to and/or receive MR signals from at least one portion of a subject being scanned. The body coil and/or the local coil may include a transmitting coil and a receiving coil. The transmitting coil may emit excitation signals (e.g., RF pulse signals) that may excite nuclei in the subject. The receiving coil may receive MR signals (e.g., MR echo signals) emitted from the subject. As shown in FIG. 2B, the transmitting coil 212-3 may be configured to emit RF pulse signals to excite nuclei in the subject. The receiving coil 212-4 may be configured to receive and/or detect MR signals emitted from the subject. In some embodiments, the transmitting coil and the receiving coil may be integrated to a single RF coil, for example, the body coil or the local coil. In some embodiments, the transmitting coil and the receiving coil may be disposed in different RF coils. For example, the transmitting coil 212-3 may be the body coil, and the receiving coil may be the local coil. The receiving coil may include a phased array coil set as a 4-channel mode, an 8-channel mode, a 16-channel mode, a 24-channel mode, or a 32-channel mode. The receiving coil may be integrated into a local RF coil device to detect the MR signals. The local RF coil device may be detachably connected to the scanning bed 213. The local RF coil device may be a wearable local RF coil device for detecting the MR signals associated with the subject. For example, the wearable local RF coil device may include a plurality of RF local coils attached to a region of interest (ROI) of the subject (e.g., a chest, a head, a breast, a spine, a knee, an ankle, etc.). As described in connection with FIG. 2A, the subject 214 may be supported on the table of the scanning bed 213, and a local RF coil device for detecting MR signals from the spine (e.g., a spine coil device) may be disposed under the back of the subject. During the scan process, the spine coil device may be configured to detect MR signals emitted from the spine, and send the detected MR signals to the controller 222 for further processing.

As shown in FIG. 2B, inside the main magnetic body 212-1, for example, cylinder-shaped, the gradient coil 212-2 may be arranged so as to become coaxial with the main magnetic body 212-1. The transmitting coil 212-3, for example, the body coil, may be disposed in the space encircled by the main magnetic body 212-1 and the gradient coil 212-2. The main magnetic body 212-1, the gradient coil 212-2 and the body coil may form the cavity extending along the X direction. In some embodiments, the space in the cavity may be designated as a detecting space or an imaging space, for example, a region which is set as a part of the imaging space and is a range of acquisition of MR signals used to generate "one image" or "one set of images." The central region of the cavity may correspond to the FOV region.

As used herein, as described with FIG. 2A and FIG. 2B, for an MRI system or an MRI device, one or more components of the MRI device may be classified to a coil side assembly and a system side assembly. The coil side assembly may include one or more RF receiving coils for detecting MR signals from at least part of the subject. For example, the coil side assembly may include a local RF coil device including the RF receiving coil 212-4. Descriptions regarding the coil side assembly may be found elsewhere in the present disclosure (e.g., FIG. 3, FIG. 11, FIG. 12, or FIGS. 14-17, and the descriptions thereof). The components other than the coil side assembly may be included in the system side assembly which is separate from the coil side assembly. The system side assembly may include one or more components for scanning the at least part of the subject, generating MR signals associated with the at least part of the subject, and processing the MR signals received from the coil side assembly. For example, the system side assembly may include the main magnetic body 212-1, the gradient coil 212-2, the transmitting coil 212-3, and the controller 222. Descriptions regarding the system side assembly may be found elsewhere in the present disclosure (e.g., FIG. 3, FIG. 11, FIG. 12, or FIGS. 14-17, and the descriptions thereof).

The main magnetic body of the system side assembly may provide a uniform static magnetic field. The gradient coil of the system side assembly may provide the gradient field. The transmitting coil of the system side assembly may transmit RF pulses to excite the nuclei to generate MR signals (e.g., MR echo signals). The MR signals may be encoded by the gradient coil. The RF receiving coil of the coil side assembly may receive the encoded MR signals, and send the MR signals to the controller of the system side assembly via the network (e.g., the wireless network). The controller may reconstruct an MR image by processing the received MR signals. In some embodiments, to wirelessly send the MR signals to the controller, the RF receiving coil may be a wireless-type RF coil, which employs an internal receiver clock (hereinafter local clock). A local clock generator may produce the local clock signal for operation timing of the RF receiving coil. For example, in response to the local clock signal, the wireless RF coil may acquire analog MR signals during an acquisition period. In some embodiments, a system clock generator may generate a system clock signal which is a reference of the whole operation timing of the MRI device. However, in some cases, when the local clock is not accurately synchronize with the system clock, the MR signals acquired by the RF receiving coil may include phase noises caused by the local clock during the acquisition period. The MR signals between the coil side assembly and the system side assembly may not be synchronized. The controller may reconstruct the MR image having image artifacts due to the MR signals including phase noises.

Figure 3:
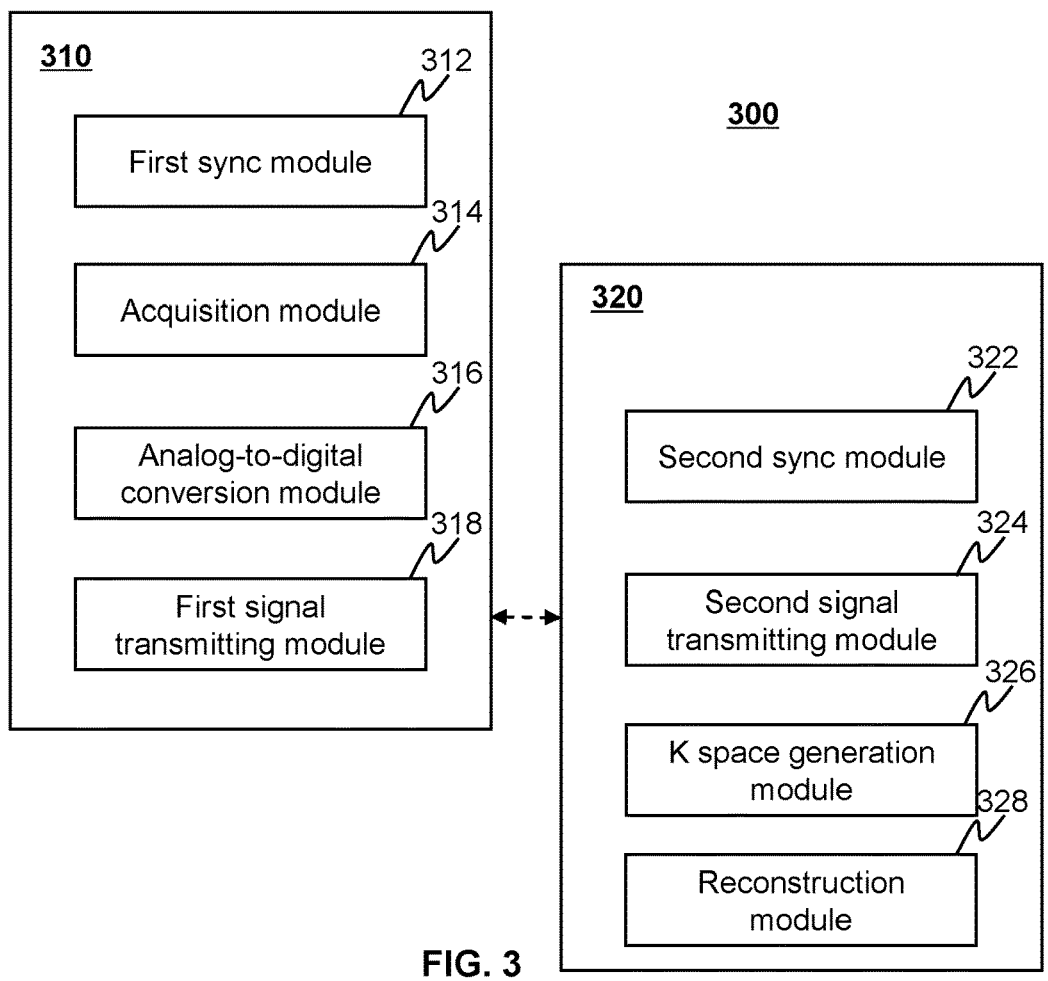
FIG. 3 is a block diagram illustrating exemplary components of a coil side assembly and a system side assembly of an MRI system according to some embodiments of the present disclosure.

FIG. 3 is a block diagram illustrating exemplary components of a coil side assembly and a system side assembly of an MRI system. As shown in FIG. 3, MRI system 300 may include a coil side assembly 310 and a system side assembly 320. The coil side assembly 310 may include a first sync module 312, an acquisition module 314, an analog-to-digital conversion module 316 and a first transmitting module 318. The system side assembly 320 may include a second sync module 322, a second signal transmitting module 324 and a reconstruction module 328.

The modules may be hardware circuits of at least part of a processing device or a controller. The modules may also be implemented as an application or set of instructions read and executed by a processing device in the coil side assembly 310 and/or the system side assembly 320. Further, the modules may be any combination of the hardware circuits and the application/instructions. For example, the modules may be the part of the processing device in the coil side assembly 310 and/or the system side assembly 320 when the processing device is executing the application/set of instructions.

In some embodiments, a system clock generator may be operably coupled with the system side assembly 320. The system clock generator may generate a system clock signal having a predetermined frequency. The system clock signal may be designated as a reference for the whole operation timing of the MRI system. In some embodiments, a local clock generator may be operably coupled with a local RF coil device including a plurality of RF receiving coils. The local clock generator may generate a local clock signal that controls the operation timing of the receiving coil, for example, the local clock signal may indicate when to acquire MR echo signals during the scan period. For MRI, a stable reference clock (e.g., the system clock) may be needed in order to ensure that all local clocks regarding the plurality of receiving coils run at the same rate. In some cases, because of the wireless nature of wireless receiving coil (e.g., inevitable time delays), it is often difficult to accurately synchronize the local clock with the system clock.

To resolve the issue or a similar issue above, the first sync module 312 may determine the time difference between the local clock and the system clock. For example, the first sync module 312 may determine a time delay in the local clock generator compared to the system clock generator. The first sync module 312 may further determine the time difference based on the time delay. In some embodiments, the first sync module 312 may further correct the local clock generator based on the time difference, so as to maintain a constant phase difference between clock signals generated by the local clock generator and by the system clock generaton.

In some embodiments, the first sync module 312 may interact with the second sync module 322 by using one or more Sync messages or other reference signals. For example, the first sync module 312 may generate one or more Sync messages to the second sync module 322, and receive one or more Sync messages sent by the second sync module 322.

Figure 5:
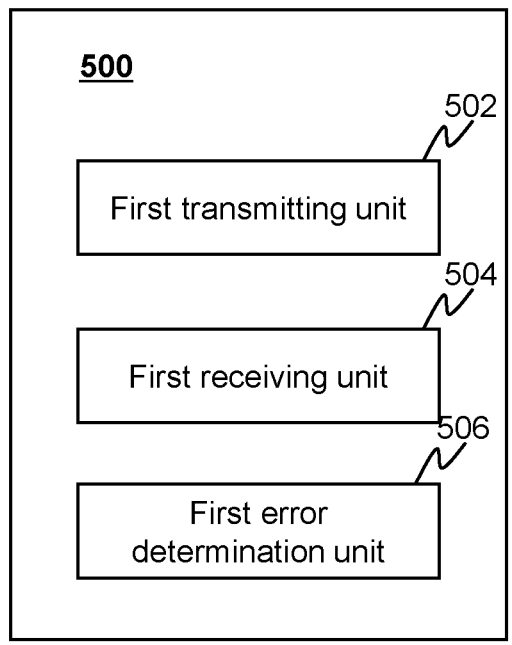
FIG. 5 is a block diagram illustrating an exemplary sync module according to some embodiments of the present disclosure.

FIG. 5 illustrates an exemplary sync module according to some embodiments of the present disclosure. The sync module 500 may be an example of the first sync module 312. As illustrated in FIG. 5, the sync module 500 may include a first transmitting unit 502, a first receiving unit 504, and a first error determination unit 506. In some embodiments, the first transmitting unit 502 may send a first Sync message to the system side assembly (e.g., the second sync module 322) via the network. The first Sync message may include a first timestamp recording when the first Sync message is sent by the coil side assembly. The first receiving unit 504 may receive a second Sync message from the system side assembly (e.g., the second sync module 322). In some embodiments, the second Sync message may include the first timestamp, a second timestamp recording when the first Sync message is received by the system side assembly, and a third timestamp recording when the second Sync message is sent by the system side assembly. The first error determination unit 506 may determine a time delay based on the first timestamp, the second timestamp, the third timestamp, and the fourth timestamp. The first error determination unit 506 may further determine a time difference based on the time delay. More descriptions regarding the determination of time difference may be found elsewhere in the present disclosure (e.g., FIGS. 8A-8B, and the descriptions thereof).

Figure 6:
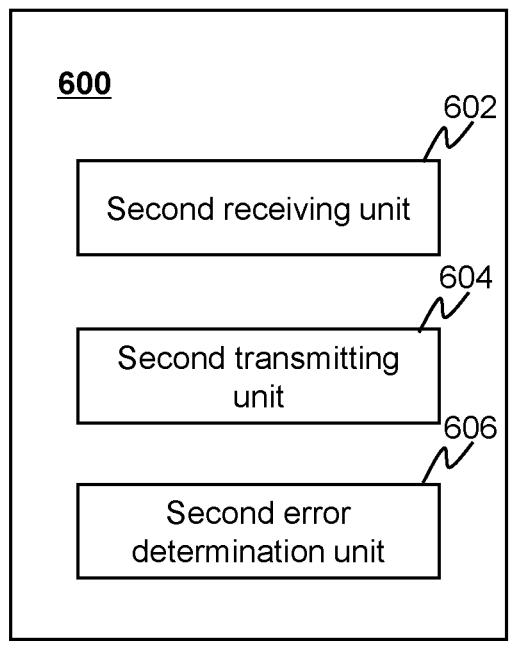
FIG. 6 is a block diagram illustrating another exemplary sync module according to some embodiments of the present disclosure.

FIG. 6 illustrates an exemplary sync module according to some embodiments of the present disclosure. The sync module 600 may be an example of the first sync module 312. As illustrated in FIG. 6, the sync module 600 may include a second receiving unit 602, a second transmitting unit 604, and a second error determination unit 606. In some embodiments, the second receiving unit 602 may receive a first Sync message from the system side assembly (e.g., the second sync module 322), and register a first timestamp recording when the first Sync message is received by the coil side assembly. The second receiving unit 602 may also receive a second Sync message from the system side assembly (e.g., the second sync module 322). The second Sync message may include a second timestamp recording when the first Sync message is sent by the system side assembly. The second transmitting unit 604 may send a third Sync message to the system side assembly (e.g., the second sync module 322), and register a third timestamp recording when the third Sync message is sent by the coil side assembly. The first receiving unit 602 may receive a fourth Sync message from the system side assembly (e.g., the second sync module 322). The fourth Sync message may include a fourth timestamp recording when the third Sync message is received by the system side assembly. The second error determination unit 606 may determine a time delay based on the first timestamp, the second timestamp, the third timestamp, and the fourth timestamp. The second error determination unit 606 may further determine a time difference based on the time delay. More descriptions regarding the determination of time difference may be found elsewhere in the present disclosure (e.g., FIGS. 9A-9B, and the descriptions thereof).

The acquisition module 314 may acquire MR echo signals by scanning at least a part of the subject in response to the clock signal generated by the corrected local clock generator. In some embodiments, a synchronization process between the local clock and the system clock may be performed before the at least part of the subject is scanned, so that the system clock generated by the system clock generator may keep synchronized with the local clock signal generated by the local clock generator. In some embodiments, the acquisition module 314 may record time information regarding the MR echo signals. In some embodiments, the time information may include acquisition time of each MR echo signal, and the time difference in the local clock generator at the coil side assembly compared to the system clock generator at the system side assembly. For example, the acquisition module 314 may obtain the time difference from the first sync module 312.

Figure 4:
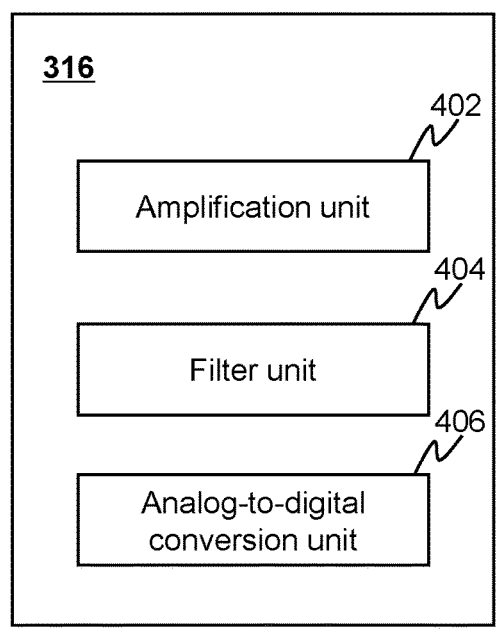
FIG. 4 is a block diagram illustrating an exemplary an analog-to-digital conversion module according to some embodiments of the present disclosure.

The analog-to-digital conversion module 316 may digitize the MR echo signal at the coil side assembly. The analog-to-digital conversion module 316 may include one or more components for digitizing the MR echo signal. FIG. 4 illustrates an exemplary an analog-to-digital conversion module according to some embodiments of the present disclosure. As illustrated in FIG. 4, the analog-to-digital conversion module 316 may include an amplification unit 402, a filter unit 404 and an analog-to-digital conversion unit 406. In some embodiments, the RF receiving coil may acquire the MR echo signals in real time or substantially real time. The amplification unit 402 may amplify the received MR echo signals to generate amplified MR echo signals. The filter unit 404 may further filter the amplified MR echo signals to generate filtered MR echo signals. The analog-to-digital conversion unit 406 may digitize the filtered MR echo signals to generate corresponding digital data.

The first signal transmitting module 318 may wirelessly send the acquired MR echo signals and/or the time information from the coil side assembly to the second signal transmitting module 324 of the system side assembly 320. In some embodiments, upon receipt of the MR echo signals and the time information, the K space generation module 326 may generate K space data based on the MR echo signals and the time information. In some embodiments, the reconstruction module 328 may reconstruct an MR image based on the K space data. In some embodiments, the K space generation module 326 may reconstruct the MR image by using a reconstruction algorithm. Exemplary reconstruction algorithms may include a Backprojection technique, a Filtered Backprojection technique, an Algebraic reconstruction technique, a model-based reconstruction technique (e.g., a machine learning model), or the like, or any combination thereof.

It should be noted that the above description is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure. For example, the coil side assembly 310 and/or the system side assembly 320 may further include a storage module (not shown in FIG. 3). The storage module may be configured to store data generated during any process performed by any component of in the coil side assembly 310 and/or the system side assembly 320.

Figure 7:
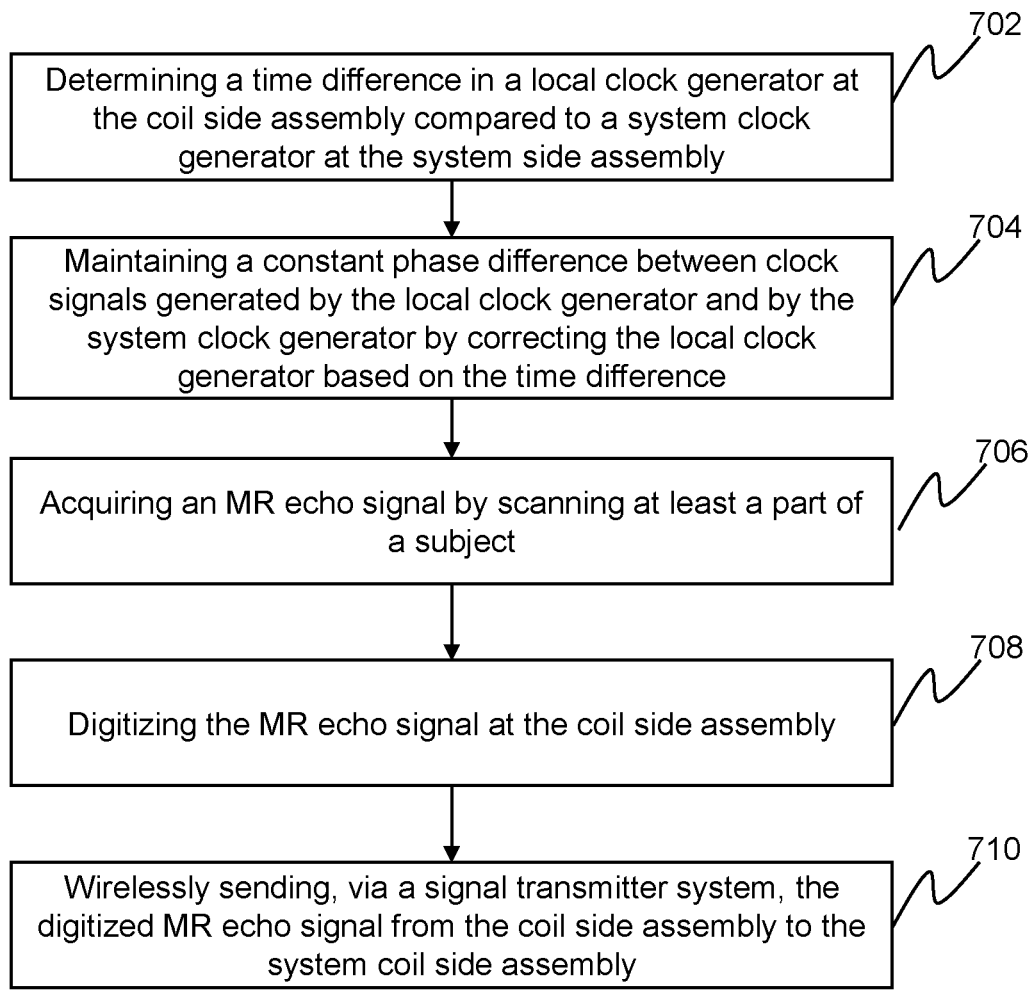
FIG. 7 is a flowchart illustrating an exemplary process for magnetic resonance (MR) signal synchronization between a coil side assembly and a system side assembly of an MRI device according to some embodiments of the present disclosure.

FIG. 7 is a flowchart illustrating an exemplary process for magnetic resonance (MR) signal synchronization between a coil side assembly and a system side assembly of an MRI device according to some embodiments of the present disclosure. One or more operations of process 700 may be implemented in imaging system 200 as illustrated in FIGS. 2A and 2B. For example, the process 700 may be stored in a storage device of the imaging system 200 in the form of instructions, and invoked and/or executed by at least one processing component (e.g., one or more modules of the coil side assembly 310 and/or the system side assembly 320). In some embodiments, the process 700 may be accomplished with one or more additional operations not described, and/or without one or more of the operations discussed. Additionally, the order in which the operations of the process 700 as illustrated in FIG. 7 and described above is not intended to be limiting.

In 702, a processing component (e.g., the first sync module 312 at the coil side assembly 310) may determine a time difference in a local clock generator at the coil side assembly compared to a system clock generator at the system side assembly.

In some embodiments, the system clock generator may be operably coupled with the system side assembly, for example, the system clock generator may be integrated to the controller 222 illustrated in FIG. 2A. The system clock generator may generate a system clock signal having a predetermined frequency. The system clock signal may be designated as a reference for the whole operation timing of the MRI device. For example, the system clock signal may indicate when to scan the subject according to a scan sequence input by a user. In some embodiments, the local clock generator may be operably coupled with a local RF coil device including a plurality of RF receiving coils. In some embodiments, each of the plurality of RF receiving coils may be operably coupled to one local clock generator. In some embodiments, the plurality of RF receiving coils may be operably coupled to one local clock generator. The local clock generator may generate a local clock signal that controls the operation timing of the receiving coil, for example, the local clock signal may indicate when to acquire MR echo signals during the scan period. For MRI, a stable reference clock (e.g., the system clock) may be needed in order to ensure that all local clocks regarding the plurality of receiving coils run at the same rate. In some cases, because of the wireless nature of wireless receiving coil (e.g., inevitable time delays), it is often difficult to accurately synchronize the local clock with the system clock. To resolve this issue or a similar issue, the processing component may determine the time difference between the local clock and the system clock, and correct the local clock generator based on the time difference. For example, the processing component may determine a time delay in the local clock generator compared to the system clock generator. The processing component may further determine the time difference based on the time delay. In some embodiments, the processing component may determine the time delay based on the transmission of reference signals (e.g., Sync messages) between the coil side assembly and the system side assembly over the network. More descriptions about determinations regarding the time delay and the time difference may be found elsewhere in the present disclosure (e.g., FIGS. 8A-9B, and the descriptions thereof).

In 704, the processing component (e.g., the first sync module 312 at the coil side assembly 310) may maintain a constant phase difference between clock signals generated by the local clock generator and by the system clock generator by correcting the local clock generator based on the time difference. In some embodiments, the processing component may correct the local clock signal generated by the local clock generator based on the time difference, so as to keep the local clock synchronized with the system clock. It should be noted that if the local clock keeps synchronized with the system clock, the phase difference between the local lock and the system lock may remain constant. In this case, in response to the local clock synchronized with the system clock, the RF receiving coil may acquire MR echo signals emitted from at least part of the subject synchronously. In some embodiments, the receiving coil may be an RF receiving set including multiple coils. Multiple MR echo signals emitted from at least part of the subject may be synchonously detected by the RF receiving coil set.

Merely for illustration, let time difference be $T_{error}$, and a timing of a local clock be $T_{local}$. The time difference may be a positive or negative value. The timing of the local clock may be corrected based on the time difference. Let the corrected timing of the local clock be $T_{correct}$. The corrected timing of the local clock may be equal to a sum of the time difference and the timing of the local clock, that is, $T_{correct}=T_{local}+T_{error}$.

In 706, a processing component (e.g., the acquisition module 314 at the coil side assembly) may acquire MR echo signals by scanning at least a part of the subject in response to the clock signal generated by the corrected local clock generator.

In some embodiments, the synchronization process between the local clock and the system clock may be performed before the at least part of the subject is scanned, so that the system clock generated by the system clock generator may keep synchronized with the local clock signal generated by the local clock generator. Merely for illustration, the controller 222 may obtain scan sequences (e.g., the RF pulse sequence, the Gx gradient sequence, the Gy gradient sequence or the Gz gradient sequence as shown in FIG. 1A) from a storage device of the MRI device. In response to one or more system clocks, the controller 222 may control one or more of the main magnetic body 212-1, the gradient coil 212-2, and/or the transmitting coil 212-3 to produce MR signals, (e.g., analog MR echo signals) based on the scan sequences. The RF receiving coil 212-4 may acquire the analog MR echo signals.

In 708, a processing component (e.g., the analog-to-digital conversion module 316 at the coil side assembly) may digitize the MR echo signal at the coil side assembly.

In some embodiments, the RF receiving coil may acquire the MR echo signals in real time or substantially real time. The processing component may amplify the received MR echo signals to generate amplified MR echo signals by using an amplifier. The processing component may filter the amplified MR echo signals to generate filtered MR echo signals by using a filter. The processing component may digitize the filtered MR echo signals to generate corresponding digital data (e.g., K space data) by performing the analog to digital conversion.

In 710, a processing component (e.g., the first signal transmitting module 318 at the coil side assembly) may wirelessly send, via a signal transmitter system, the digitized MR echo signals from the coil side assembly to the system side assembly.

In some embodiments, the coil side assembly may include a first portion of the signal transmitter system (hereinafter a first signal transmitter), and the system side assembly may include a second portion of the signal transmitter system (hereinafter a second signal transmitter). The first signal transmitter may wirelessly transmit the digitized MR echo signals to the second signal transmitter. In some embodiments, the wireless communication network between the first signal transmitter and the second signal transmitter may include near field communication (NFC), Bluetooth, WIFI, 3G, 4G, 5G, or GPRS, etc. More descriptions about the first signal transmitter and the second signal transmitter may be found elsewhere in the present disclosure (e.g., FIGS. 14-15, and the descriptions thereof).

As described with operations illustrated in FIG. 7, before each scanning of the at least part of the subject, the local clock generator of the coil side assembly may be corrected so as to keep synchronized with the system clock generator of the system side assembly. After the synchronization, the system side assembly may scan the subject, then the coil side assembly may acquire analog MR echo signals regarding the subject in response to the local clock generated by the corrected local clock generator. The analog MR echo signals may be converted to the digital MR echo signals by performing analog-to-digital conversion. The digital MR echo signals may be wirelessly sent to the system side assembly via the signal transmitter system. The signal wireless transmission may reduce the cost of using conventional RF wires or optical fibers to connect the coil side assembly and the system side assembly, and improve convenience of scanning operation to some extent.

It should be noted that the above description is merely provided for the purpose of illustration, and not intended to limit the scope of the present disclosure. For persons having ordinary skills in the art, multiple variations and modifications may be made under the teachings of the present disclosure. For example, operation 702 and operation 704 may be integrated to a single operation. However, those variations and modifications do not depart from the scope of the present disclosure.

Figure 8A:
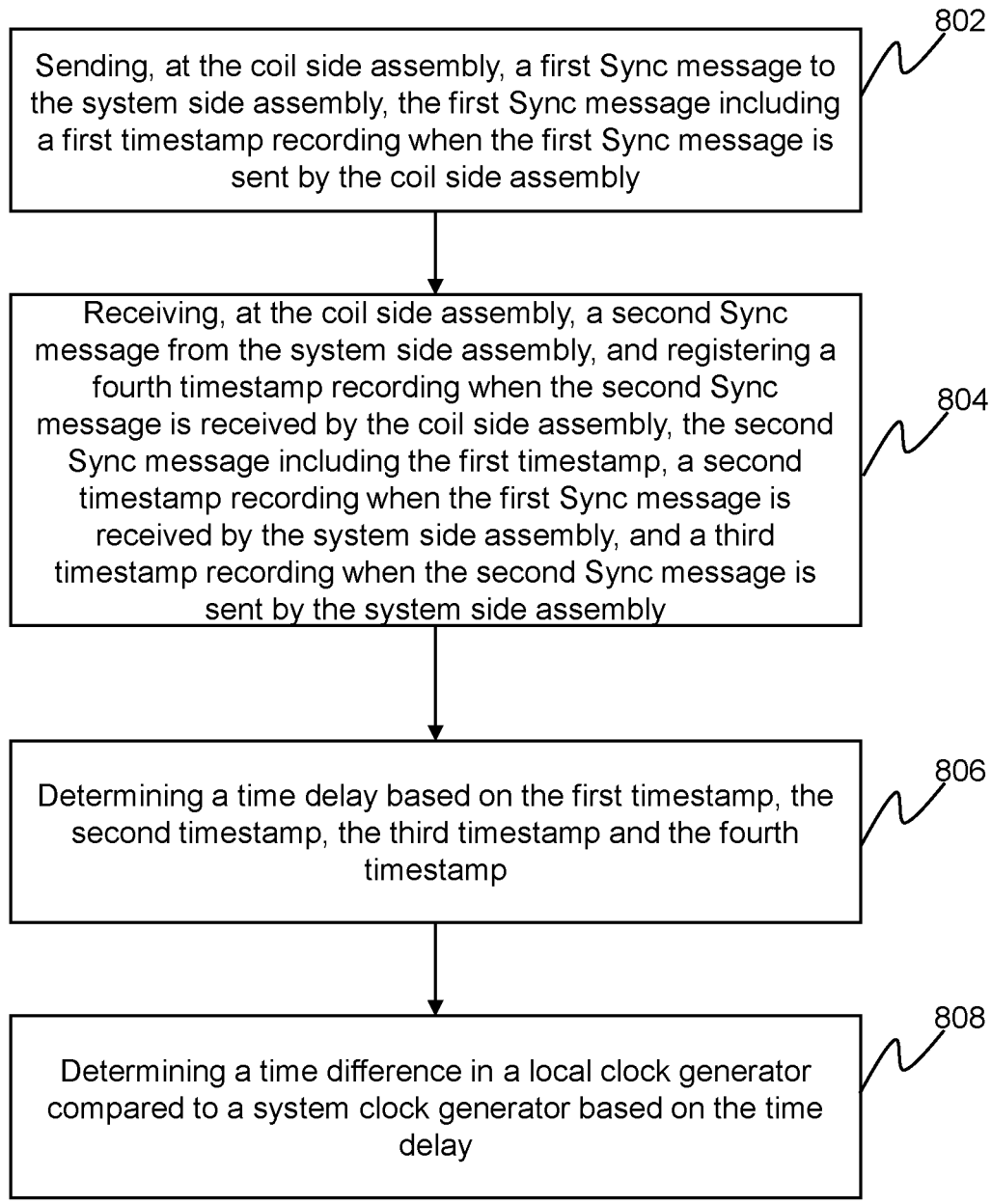
FIG. 8A is a flowchart illustrating an exemplary process for determining a time difference in a local clock generator compared to a system clock generator according to some embodiments of the present disclosure.

FIG. 8A is a flowchart illustrating an exemplary process for determining a time difference in a local clock generator compared to a system clock generator according to some embodiments of the present disclosure. One or more operations of process 800 may be implemented in imaging system 200 as illustrated in FIGS. 2A and 2B. For example, the process 800 may be stored in a storage device of the MRI system in the form of instructions, and invoked and/or executed by at least one processing component (e.g., one or more modules of the coil side assembly 310 and/or the system side assembly 320). In some embodiments, the process 800 may be accomplished with one or more additional operations not described, and/or without one or more of the operations discussed. Additionally, the order in which the operations of the process 800 as illustrated in FIG. 8A and described above is not intended to be limiting.

In 802, a processing component (e.g., the first sync module 312 at the coil side assembly 310) may send a first Sync message to the system side assembly via the network. The first Sync message may include a first timestamp recording when the first Sync message is sent by the coil side assembly (e.g., t1 shown in FIG. 8B). In some embodiments, the first Sync message may refer to a first reference signal generated by the coil side assembly.

In 804, the processing component (e.g., the first sync module 312 at the coil side assembly 310) may receive a second Sync message from the system side assembly.

In some embodiments, after the system side assembly receives the first Sync message, the system side assembly may send the second Sync message to the coil side assembly. In some embodiments, the second Sync message may refer to a second reference signal generated by the system side assembly. The second reference signal may be generated by the system side assembly in response to the first reference signal. The processing component may receive the second Sync message, and register a fourth timestamp recording when the second Sync message is received by the coil side assembly (e.g., t4 shown in FIG. 8B). In some embodiments, the second Sync message may include the first timestamp, a second timestamp recording when the first Sync message is received by the system side assembly (e.g., t2 shown in FIG. 8B), and a third timestamp recording when the second Sync message is sent by the system side assembly (e.g., t3 shown in FIG. 8B). In some embodiments, the processing component may parse the second Sync message to obtain the first timestamp, the second timestamp, and the third timestamp.

In 806, the processing component (e.g., the first sync module 312 at the coil side assembly 310) may determine a time delay based on the first timestamp, the second timestamp, the third timestamp, and the fourth timestamp. In some embodiments, the time delay may refer to a transmission delay between the coil side assembly and the system side assembly. The time delay may be designated as the transmission delay between clock signals generated by the local clock generator and the system clock generator, respectively.

Figure 8B:
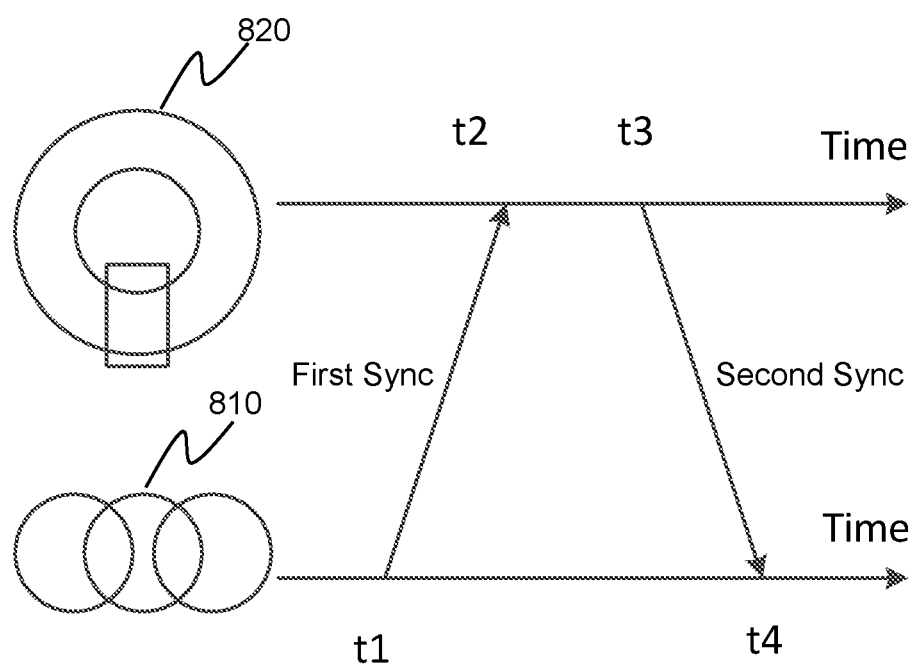
FIG. 8B is a schematic diagram illustrating an exemplary Sync message transmission between the coil side assembly and the system side assembly according to some embodiments of the present disclosure.

FIG. 8B illustrates an exemplary Sync message transmission between the coil side assembly and the system side assembly according to some embodiments of the present disclosure. As shown in FIG. 8B, reference numeral 810 denotes the coil side assembly, reference numeral 820 denotes the system side assembly, t1 denotes the first timestamp recording when the first Sync message is sent by the coil side assembly, t2 denotes the second timestamp recording when the first Sync message is received by the system side assembly, t3 denotes the third timestamp recording when the second Sync message is sent by the system side assembly, and t4 denotes the fourth timestamp recording when the second Sync message is received by the coil side assembly. In some embodiments, the processing component may determine the time delay according to Equation (1) as follows:

$$T_{delay}=[(t4-t1)-(t3-t2)]/2, \quad (1)$$

where $T_{delay}$ denotes the time delay.

In 808, the processing component (the first sync module 312 at the coil side assembly 310) may determine a time difference in the local clock generator compared to the system clock generator based on the time delay. Specifically, the processing component may determine the time difference according to Equation (2) as follows:

$$T_{error}=t2-t1-T_{delay}=[(t2-t1)+(t3-t4)]/2, \quad (2)$$

where $T_{error}$ denotes the time difference.

In some embodiments, the local clock generator may be corrected based on the determined time difference (i.e., $T_{error}$). For example, let a timing of a local clock be $T_{local}$. The time difference may be a positive or negative value. The timing of a local clock generator may be corrected based on the time difference. Let the corrected timing of the local clock be $T_{correct}$. The corrected timing of the local clock may be equal to a sum of the time difference and the timing of the local clock, that is, $T_{correct}=T_{local}+T_{error}$. After the correction, the local clock may keep synchronized with the system clock, the phase difference between the local lock and the system lock may remain constant.

Figure 9A:
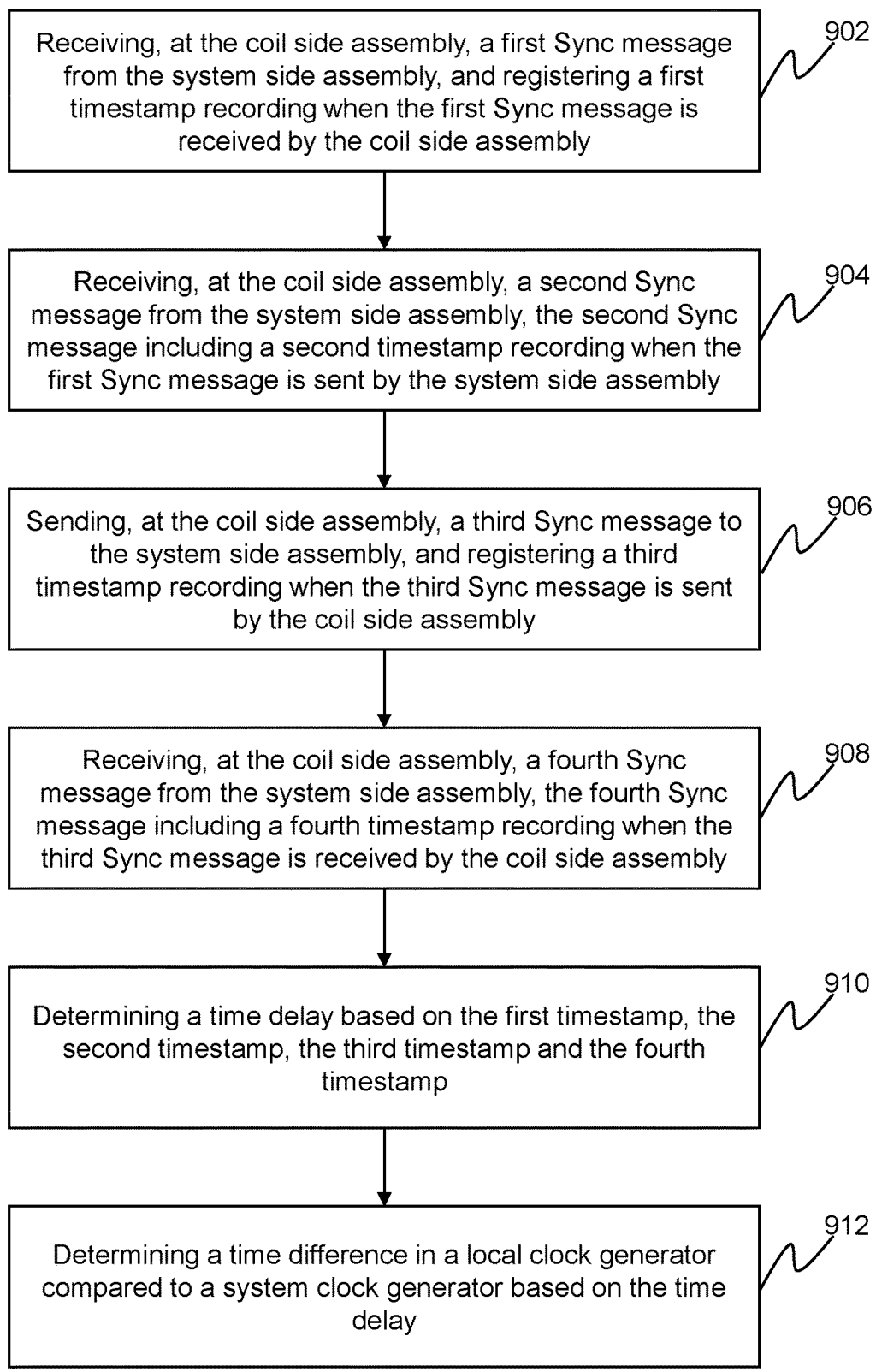
FIG. 9A is a flowchart illustrating an exemplary process for determining a time difference in a local clock generator compared to a system clock generator according to some embodiments of the present disclosure.

FIG. 9A is a flowchart illustrating an exemplary process for determining a time difference in a local clock generator compared to a system clock generator according to some embodiments of the present disclosure. One or more operations of process 900 may be implemented in imaging system 200 as illustrated in FIGS. 2A and 2B. For example, the process 900 may be stored in a storage device of the MRI system in the form of instructions, and invoked and/or executed by at least one processing component (e.g., one or more modules of the coil side assembly 310 and/or the system side assembly 320). In some embodiments, the process 900 may be accomplished with one or more additional operations not described, and/or without one or more of the operations discussed. Additionally, the order in which the operations of the process 900 as illustrated in FIG. 9A and described above is not intended to be limiting.

Figure 9B:
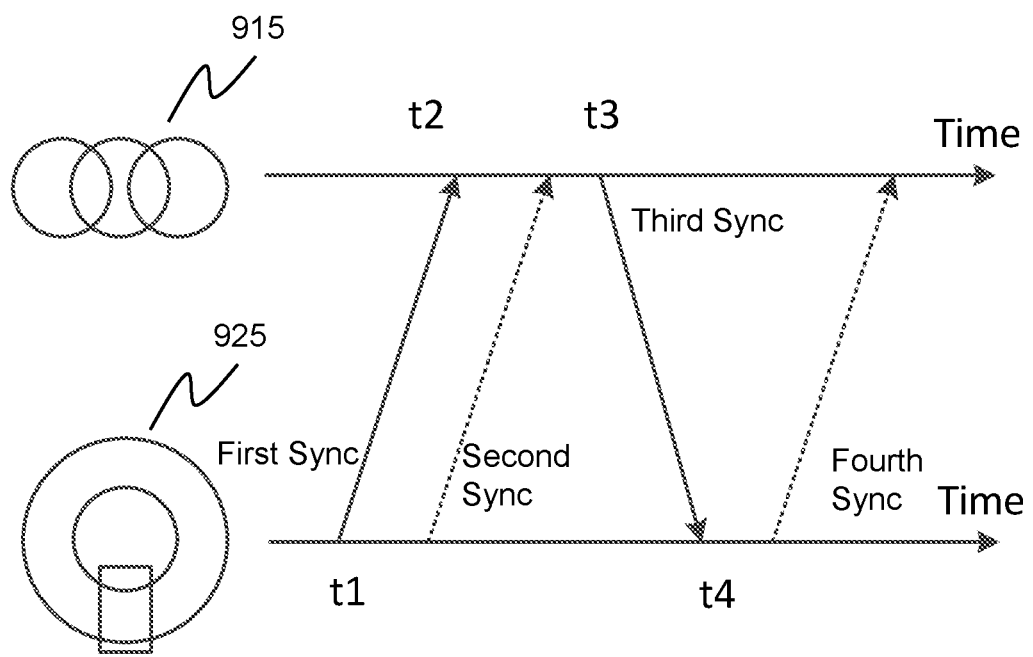
FIG. 9B is a schematic diagram illustrating an exemplary Sync message transmission between the coil side assembly and the system side assembly according to some embodiments of the present disclosure.

In 902, a processing component (e.g., the first sync module 312 at the coil side assembly 310) may receive a first Sync message from the system side assembly, and register a first timestamp recording when the first Sync message is received by the coil side assembly (e.g., t2 shown in FIG. 9B).

In some embodiments, the system side assembly may send the first Sync message to the coil side assembly. The coil side assembly may register the first time timestamp recording when the first Sync message is received. In some embodiments, the first Sync message may refer to a first reference signal generated by the system side assembly.

In 904, the processing component (e.g., the first sync module 312 at the coil side assembly 310) may receive a second Sync message from the system side assembly. The second Sync message may include a second timestamp recording when the first Sync message is sent by the system side assembly (e.g., t1 shown in FIG. 9B). The processing component may parse the second Sync message to obtain the second timestamp.

In 906, the processing component (e.g., the first sync module 312 at the coil side assembly 310) may send a third Sync message to the system side assembly, and register a third timestamp recording when the third Sync message is sent by the coil side assembly (e.g., t3 shown in FIG. 9B).

In some embodiments, after the processing component receives the first Sync message from the system side assembly, the processing component may send the third Sync message as a response to the system side assembly. The processing component may save the timestamp recording when the third Sync message is sent by the coil side assembly as the third timestamp.

In 908, the processing component (e.g., the first sync module 312 at the coil side assembly 310) may receive a fourth Sync message from the system side assembly. The fourth Sync message may include a fourth timestamp recording when the third Sync message is received by the system side assembly (e.g., t4 illustrated in FIG. 9B).

In some embodiments, the system side assembly may receive the third Sync message from the coil side assembly, and register the timestamp recording when the third Sync message is received by the system side assembly. Upon receipt of the third Sync message, the system side assembly may send the forth Sync message as a response to the coil side assembly. The coil side assembly may receive the fourth Sync message including the fourth timestamp.

In 910, the processing component (e.g., the first sync module 312 at the coil side assembly 310) may determine a time delay based on the first timestamp, the second timestamp, the third timestamp, and the fourth timestamp. In some embodiments, the time delay may refer to a transmission delay between the coil side assembly and the system side assembly. The time delay may be designated as the transmission delay between clock signals generated by both the local clock generator and the system clock generator.

FIG. 9B illustrates an exemplary Sync message transmission between the coil side assembly and the system side assembly according to some embodiments of the present disclosure. As shown in FIG. 9B, reference numeral 915 denotes the coil side assembly, reference numeral 925 denotes the system side assembly, t1 denotes the second timestamp recording when the first Sync message is sent by the system side assembly, t2 denotes the first timestamp recording when the first Sync message is received by the coil side assembly, t3 denotes the third timestamp recording when the third Sync message is sent by the coil side assembly, and t4 denotes the fourth timestamp recording when the third Sync message is received by the system side assembly. In some embodiments, the processor may determine the time delay according to Equation (3) as follows:

$$T_{delay}=[(t4-t1)-(t3-t2)]/2, \quad (3)$$

where $T_{delay}$ denotes the time delay.

In 912, the processing component (the first sync module 312 at the coil side assembly 310) may determine a time difference in the local clock generator compared to the system clock generator based on the time delay. Specifically, the processing component may determine the time difference according to Equation (4) as follows:

$$T_{error}=t2-t1-T_{delay}=[(t2-t1)+(t3-t4)]/2, \quad (4)$$

where $T_{error}$ denotes the time difference.

In some embodiments, the local clock generator may be corrected based on the determined $T_{error}$. For example, let a timing of a local clock be $T_{local}$. The time difference may be a positive or negative value. The timing of a local clock may be corrected based on the time difference. Let the corrected timing of the local clock be $T_{correct}$. The corrected timing of the local clock generator may be equal to a sum of the time difference and the timing of the local clock, that is, $T_{correct}=T_{local}+T_{error}$. After the correction, the local clock may keep synchronized with the system clock, the phase difference between the local lock and the system lock may remain constant.

As described in connection with operations 902-912, the processing component(s) may determine the time difference by performing four Sync message transmissions, which may help to determine the time difference accurately. The time synchronization between the coil side assembly and the system side assembly may be achieved by correcting the time difference.

Figure 10A:
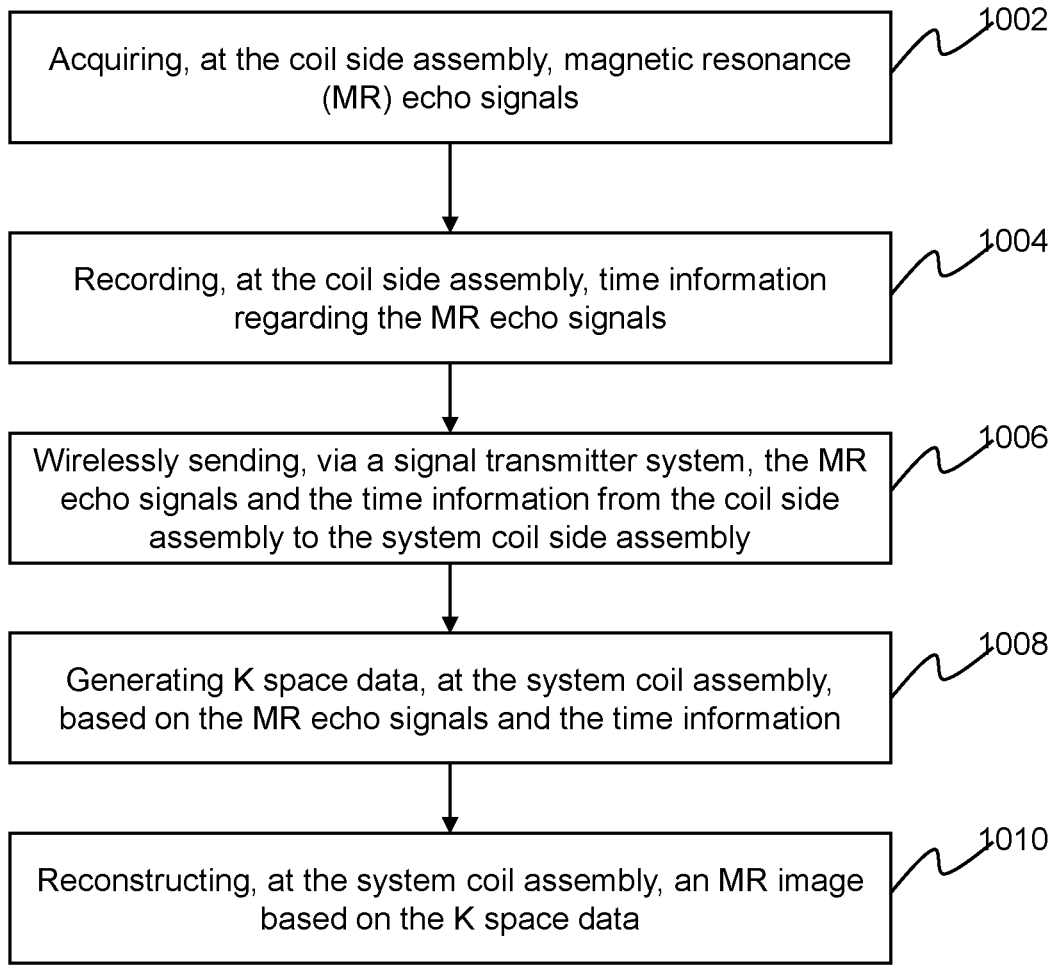
FIG. 10A a flowchart illustrating an exemplary imaging process by an MRI device according to some embodiments of the present disclosure.

FIG. 10A is a flowchart illustrating an exemplary imaging process by an MRI device according to some embodiments of the present disclosure. One or more operations of process 1000 may be implemented in imaging system 200 as illustrated in FIGS. 2A and 2B. For example, the process 1000 may be stored in a storage device of the MRI system in the form of instructions, and invoked and/or executed by at least one processing component (e.g., one or more modules of the coil side assembly 310 and/or the system side assembly 320). In some embodiments, the process 1000 may be accomplished with one or more additional operations not described, and/or without one or more of the operations discussed. Additionally, the order in which the operations of the process 1000 as illustrated in FIG. 10A and described above is not intended to be limiting.

In 1002, a processing component (e.g., the acquisition module 314 at the coil side assembly 310) may acquire MR echo signals.

In some embodiment, the MR scanner (e.g., the scanner 212 shown in FIG. 2A) may scan at least a part of a subject in accordance with one or more scan sequences (e.g., RF pulse sequences, Gx gradient sequences, Gy gradient sequences, or Gz gradient sequences as shown in FIG. 1A). During the scan period, the processing component may acquire MR echo signals emitted from the at least part of the subject via one or more RF receiving coils (e.g., the RF receiving coils included in the coil side assembly). In some embodiments, the acquired MR echo signals may be analog signals.

In 1004, the processing component (e.g., the acquisition module 314 at the coil side assembly 310) may record time information regarding the MR echo signals. In some embodiments, the time information may include acquisition time of each MR echo signal, and a time difference in a local clock generator at the coil side assembly compared to a system clock generator at the system side assembly.

In some embodiments, before the scanning, the processing component may determine time difference as described in connection with FIGS. 8A and 8B, or FIGS. 9A and 9B. For example, the first sync module 312 may determine a time delay between the local clock generator and the system clock generator according to Equation (1) or Equation (3). The first sync module 312 may further determine the time difference based on the time delay according to Equation (2) or Equation (4). The acquisition module 314 may obtain the time difference, and store the time difference in a storage device. During the scanning, when the RF receiving coils acquire an MR echo signal, the acquisition module 314 may obtain corresponding acquisition time, and store the acquisition time in the storage device. In some embodiments, the acquisition time corresponding to each echo signal may relate to a phase encoding line generated by Gy gradient sequences.

In 1006, a processing component (e.g., the first signal transmitting module 318 at the coil side assembly 310) may wirelessly send the acquired MR echo signals and the time information from the coil side assembly to the system side assembly. For example, the first signal transmitting module 318 may wirelessly, via a first signal transmitter, send the MR signals to the second signal transmitting module 324. The second signal transmitting module 324 may, via a second signal transmitter, receive the MR signals.

In 1008, a processing component (e.g., the K space generation module 326 at the system side assembly 320) may generate K space data based on the MR echo signals and the time information.

In some embodiments, a scan sequence may include an ADC (Analog to Digital Converter) acquisition window. Within the duration of the acquisition window, the analog MR echo signal may be discretely sampled at a sampling interval. In some embodiments, each sampling interval may be equal. The sampled data may be digital data. The sampled data may be filled to a corresponding location of K space. The K space data may be used to reconstruct an MR image. In some embodiments, the processing component may sample the MR echo signal based on the sampling interval and the time difference, and fill the sampled data point to the K space point in the row. The processing component may fill the acquired MR echo signal to a row of the K space based on the acquisition time.

Figure 10B:
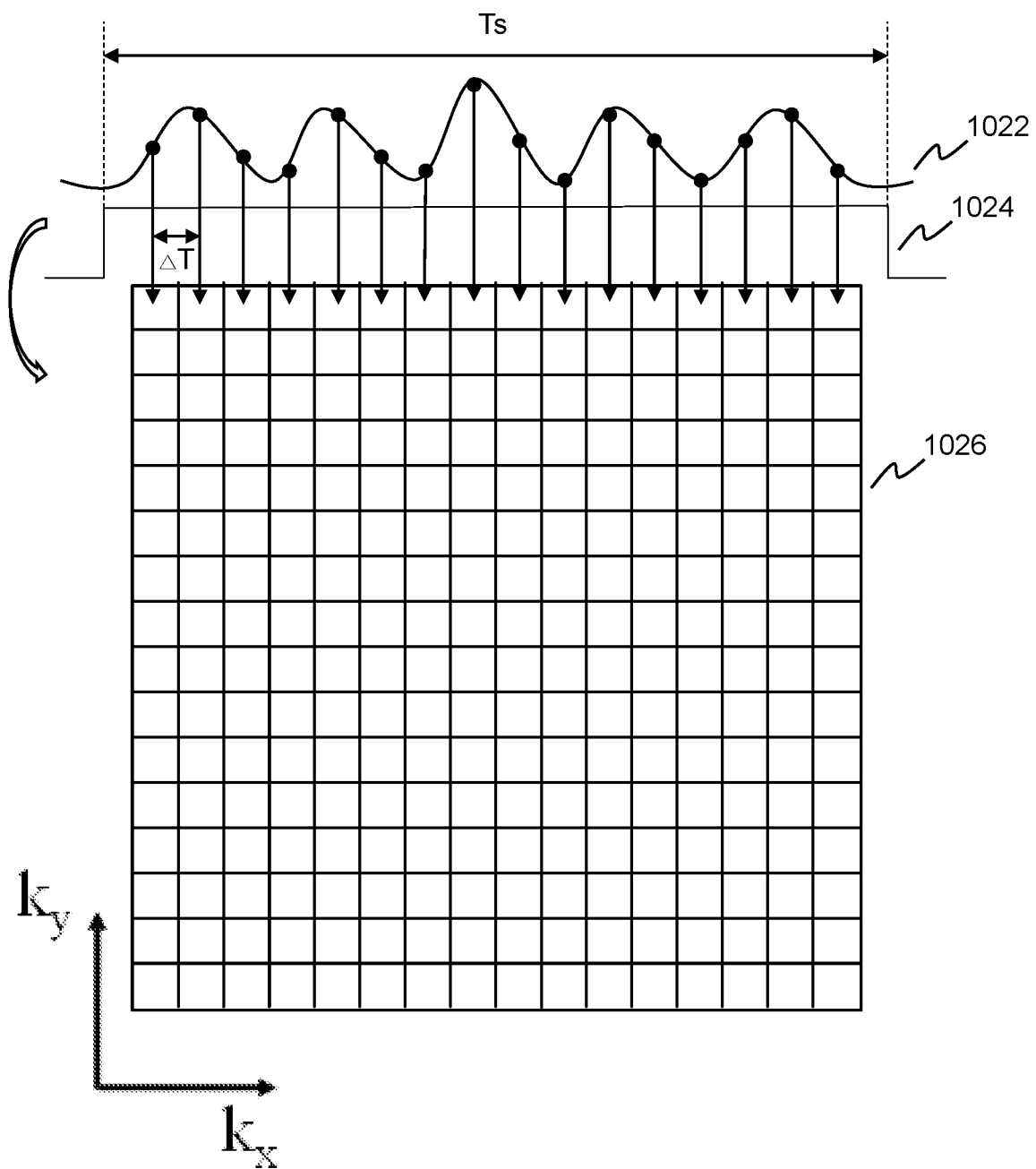
FIG. 10B is a schematic diagram illustrating an exemplary relation of an MR echo signal and K space according to some embodiments of the present disclosure.

FIG. 10B illustrates an exemplary relation of an MR echo signal and K space according to some embodiments of the present disclosure. As shown in FIG. 10B, reference numeral 1022 denotes an MR echo signal acquired by the RF receiving coil in one TR, reference numeral 1024 denotes an acquisition window, reference numeral 1026 denotes a K space. The K space 1026 may be in the form of a matrix. Each grid of the K space 1026 represents a K space data point in the matrix. Kx denotes a frequency encoding direction, and Ky denotes a phase encoding direction. Let the time length of the acquisition window be Ts. A sampling interval, $\Delta T$, may be predetermined. The processing component may sample the MR echo signal 1022 according to the sampling interval, and obtain a plurality of data points to be filled. Each sampled data point may be filled to a corresponding grid in the K space 1026. However, due to the time difference, the sampled data point may be inaccurate based on the predetermined sampling interval. The processing component may need to sample the MR echo signal based on a corrected sampling interval, so as to acquire accurate K space data. The corrected sampling interval may be equal to a sum of the predetermined sampling interval and the time difference, that is, $\Delta T + T_{error}$. The processing component may sample a plurality of data points based on the corrected sampling interval. The plurality of data points may be filled to the corresponding grids of the K space. Merely for illustration, only one MR echo signal is illustrated in FIG. 10B; however, a plurality of MR echo signals may be acquired during the scanning. In some embodiments, the acquisition time of the MR echo signal may correspond to a timing of a phase encoding sequence applied to the subject (e.g., Gy gradient sequence), and the phase encoding sequence may correspond to the location of the K space in Ky direction (e.g., a location in the row). Therefore, the processing component may fill each of the plurality of MR echo signals to the corresponding row of the K space based on the acquisition time of the MR echo signal.

In 1010, a processing component (e.g., a reconstruction module 328 at the system side assembly 320) may reconstruct an MR image based on the K space data.

In some embodiments, the processing component may reconstruct the MR image by using a reconstruction algorithm. Exemplary reconstruction algorithms may include a Backprojection technique, a Filtered Backprojection technique, an Algebraic reconstruction technique, a model-based reconstruction technique (e.g., a machine learning model), or the like, or any combination thereof.

It should be noted that the above description is merely provided for the purpose of illustration, and not intended to limit the scope of the present disclosure. For persons having ordinary skills in the art, multiple variations and modifications may be made under the teachings of the present disclosure. For example, operation 1008 and operation 1010 may be integrated into a single operation. However, those variations and modifications do not depart from the scope of the present disclosure.

Figure 11:
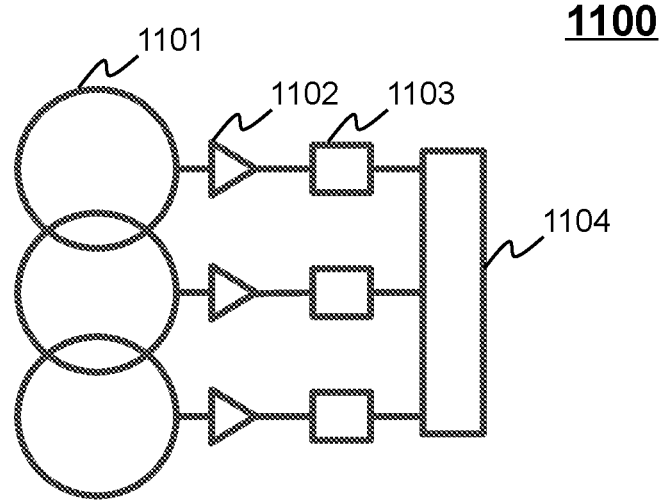
FIG. 11 is a schematic diagram illustrating an exemplary coil side assembly according to some embodiments of the present disclosure.

FIG. 11 is a schematic diagram illustrating an exemplary coil side assembly according to some embodiments of the present disclosure. As shown in FIG. 11, coil side assembly 1100 may include a plurality of radio frequency (RF) receiving coils, e.g., the RF receiving coil being the same as or similar to the RF receiving coil 1101. In some embodiments, each RF receiving coil (e.g., the RF receiving coil 1101) may be operably coupled to an amplifier (e.g., the amplifier 1102). The amplifier may be operably coupled to a first element including a filter and an analog-to-digital converter (e.g., a first element 1103). The first element 1103 may be operably connected to a second element including a processor and a signal transmitting module (e.g., a second element 1104). The amplifier 1102 may amplify MR signals (e.g., MR echo signals) acquired by the RF receiving coil 1101 so as to improve the signal to noise ratio (SNR) of the MR signals. The filter may filter the MR signals to filter out out-of-band signals. The analog-to-digital converter may convert an analog signal into a digital signal. The digital signal may be further processing by the processor included in the second element 1104. In some embodiments, an advantage of the digital signal is that the digital signal may have a strong anti-interference during the signal wireless transmission.

The second element 1104 (e.g., the processor and the signal transmitting module) may control one or more operations of the coil side assembly 1100 via Field Programmable Gata Array (FPGA) circuits, for example, receiving and/or transmitting timing or clock signals (e.g., a system clock or a local clock), or controlling the acquisition and/or digitization of the MR signals in response to requirements of the system side assembly. In some embodiments, the signal transmitting module may be a wireless transmitting module. The wireless signal transmitting module may include an up link and a down link. The wireless signal transmitting module may be configured to transmit or receive the signals from the system side assembly via the up link and the down link. For example, the system side assembly may transmit control signals and synchronization information to the coil side assembly via the up link. The coil side assembly may transmit the MR signals to the system side assembly via the down link. In some embodiments, before establishing the uplink and the down link, a synchronization confirmation process between the coil side assembly and the system side assembly may be performed. More descriptions about the synchronization confirmation process may be found elsewhere in the present disclosure (e.g., FIG. 13, and the descriptions thereof).

Figure 12:
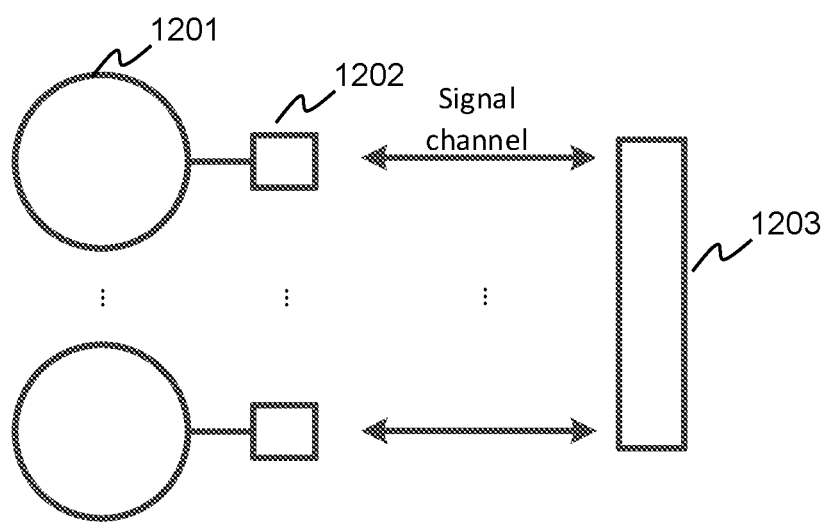
FIG. 12 is a schematic diagram illustrating an exemplary signal transmission between a coil side assembly and a system side assembly according to some embodiments of the present disclosure.

FIG. 12 is a schematic diagram illustrating exemplary signal transmission between a coil side assembly and a system side assembly according to some embodiments of the present disclosure. As shown in FIG. 12, the coil side assembly of an MRI device may include a plurality of RF receiving coils (e.g., the RF receiving coil 1201). The RF receiving coil 1201 may communicate with the system side assembly 1203 of the MRI device via a wireless signal transmitting module 1202. For example, the wireless signal transmitting module 1202 may send wireless signals to the system side assembly 1203 or receive signals from the system side assembly 1203 by using a signal channel over a network. In some embodiments, each RF receiving coil may be deemed to be a data collection node. The plurality of data collection nodes may form a node network for communicating with the system side assembly 1203. In some embodiments, since the signal transmission between the coil side assembly and the system side assembly is achieved by way of wireless communication, the system side assembly 1203 and the RF receiving coil 1201 may form a multiple access communication network system. In this system, each RF receiving coil may transmit a signal to the system side assembly via a shared signal channel. For the MRI system, since a signal synchronization needs to be satisfied, the multiple access communication network system may be implemented using a Frequency Division Multiple Access (FDMA) technique or a Code Division Multiple Access (CDMA) technique. In some embodiments, an FDMA technique may be inefficient because it occupies the signal channel only when the RF receiving coil is utilized, which may limit a transmission rate, or the number (or count) of RF receiving coils that are simultaneously connected to the network. In some embodiments, a CDMA technique may use a direct sequence spread spectrum (DSSS) mode to achieve that multiple RF receiving coils share a single channel. Each RF receiving coil may be assigned a unique feature sequence. The CDMA technique may enable the signal to be spread throughout the frequency band.

In some embodiments, the system side assembly 1203 may transmit or transfer electric energy to the plurality of RF receiving coils 1201 by means of wireless charging. In some embodiments, because a distance between the transmitting coil of the system side assembly 1203 and the RF receiving coil 1201 of the coil side assembly is relatively close, when the transmitting coil passes a current, the generated magnetic flux may produce an induced electromotive force in corresponding RF receiving coil according to the electromagnetic induction principle, then the electric energy may be transmitted to the RF receiving coil wirelessly. In some embodiments, the system side assembly 1203 may also supply electric energy to the RF receiving coil by means of microwave power transmission.

Figure 13:
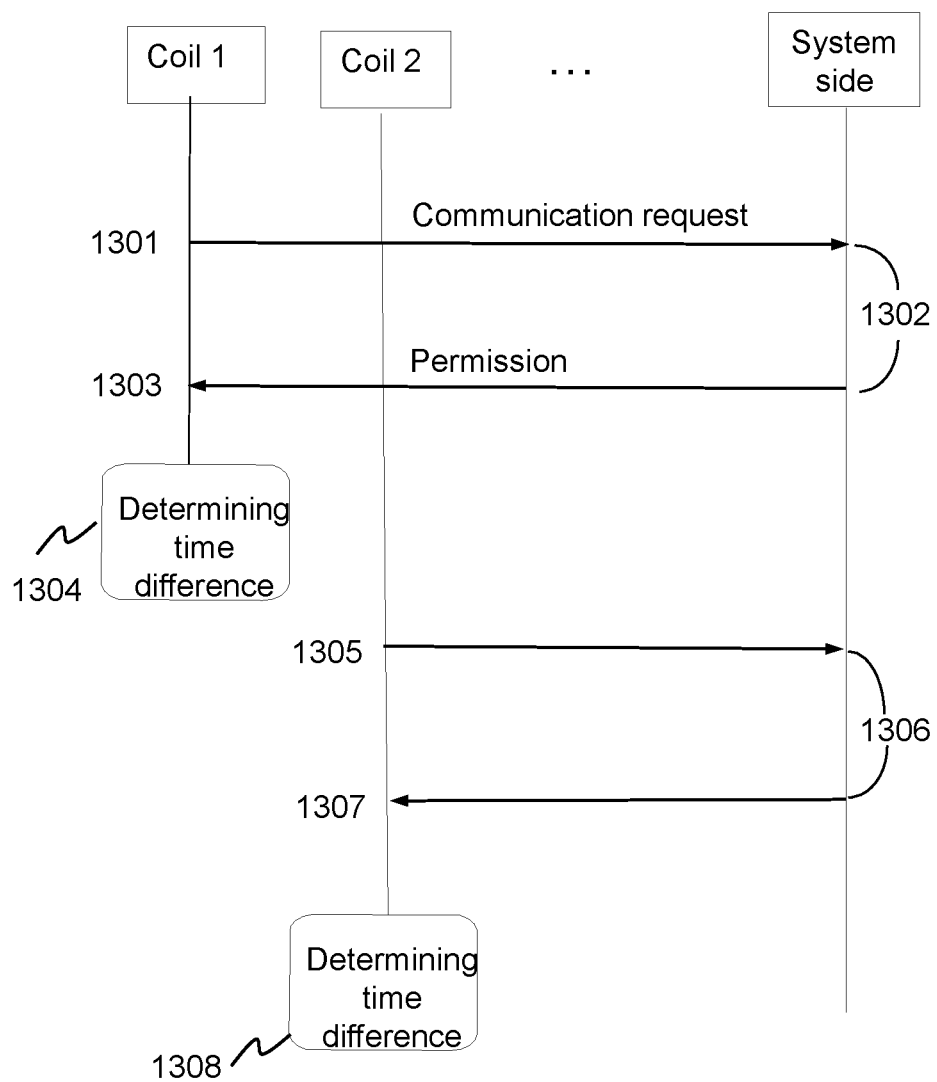
FIG. 13 is a schematic diagram illustrating an exemplary process for establishing MR signal synchronization between a coil side assembly and a system side assembly according to some embodiments of the present disclosure.

FIG. 13 is a schematic diagram illustrating an exemplary process 1300 for establishing MR signal synchronization between a coil side assembly and a system side assembly according to some embodiments of the present disclosure. In some embodiments, the coil side assembly may include a plurality of RF receiving coils. Each of the plurality of RF receiving coils may acquire MR echo signals. The RF receiving coil may wirelessly send the acquired MR echo signals to the system side assembly through a signal channel. In some embodiments, it is significant that the RF receiving coil wirelessly send the MR echo signals to the system side assembly synchronously, so as to reduce phase noises of the MR echo signals caused by the wireless network.

In 1301, the RF receiving coil (e.g., a processor coupled with the RF receiving coil 1) may, via a signal transmitter system (e.g., the wireless signal transmitting module 1202 connected to the receiving coil 1201 illustrated in FIG. 11), wirelessly send a request for communicating with the system side assembly (hereinafter the communication request) to the system side assembly.

In some embodiments, when the plurality of RF receiving coils disposed in the coil side assembly acquire MR echo signals, each RF receiving coil may monitor a transmission condition on a signal channel connected to the RF receiving coil and the system side assembly. If the transmission condition of the signal channel is idle, the RF receiving coil may send the communication request to the system side assembly.

In some embodiments, the communication request may include coil characteristic and/or time information associated with transmitting the communication request. For example, the coil characteristic may include a type of the RF receiving coil, a frequency band to which the RF receiving coil belongs, or a feature code generated by, e.g., the FDMA or the CDMA. The type of the RF receiving coil may include a birdcage coil, a solenoid coil, a saddle coil, a Helmholtz coil, a phased array coil, a transverse electromagnetic coil, or a loop coil. The time information may include a timestamp recording when the communication request is sent by the RF receiving coil (e.g., a first timestamp, t1, shown in FIG. 8B).

In 1302, the system side assembly (e.g., a processor at the system assembly) may receive the communication request, and register a timestamp recording when the request is received by the system side assembly (e.g., a second timestamp, t2, shown in FIG. 8B). In some embodiments, in response to the communication request, the system side assembly may generate a permission that enables the RF receiving coil to wirelessly send MR echo signals via an assigned signal channel.

In some embodiments, in response to the communication request and prior to generating the permission, the system side assembly may determine whether signal channel(s) is blocked or occupied. If the signal channel(s) is not blocked or occupied, the system side assembly may assign the signal channel for communication between the RF receiving coil and the system side assembly based on the coil characteristic. For example, the system side assembly may obtain the coil characteristic (e.g., the type of the receiving coil being a birdcage coil), and assign a specific signal channel for the birdcage coil using, e.g., the FDMA technique or the CDMA technique. In some embodiments, different types of RF receiving coils may correspond to different signal channels. In some embodiments, when the signal channel is assigned, the system side assembly may send the permission to the RF receiving coil. The permission may include the first timestamp, the second timestamp, a third timestamp recording when the response is sent by the system side assembly (e.g., the third timestamp, t3, shown in FIG. 8B).

In some embodiments, if the signal channel(s) is blocked or occupied, the system side assembly may send a feedback signal indicative of the blocking. The receiving request may continue to perform operation 1301, for example, sending a new communication request to the system side assembly.

In 1303, the RF receiving coil (e.g., the processor coupled with the RF receiving coil 1) may receive wirelessly, via the signal transmitter system, the permission from the system side assembly to communicate with the system side assembly, and register a timestamp recording when the permission is received by the RF receiving coil (e.g., a fourth timestamp, t4, shown in FIG. 8B).

In 1304, the receiving coil (e.g., the processor coupled with the RF receiving coil 1) may determine a time difference in the RF receiving coil compared to the system side assembly.

As described in connection with FIGS. 8A and 8B, the time difference may be determined based on the first timestamp (e.g., t1), the second timestamp (e.g., t2), the third timestamp (e.g., t3), and the fourth timestamp (e.g., t4). For example, a time delay (e.g., $T_{delay}$) may be determined based on Equation (1). The time difference (e.g., $T_{error}$) may be further determined based on the time delay and Equation (2).

In some embodiments, a local clock generator regarding the RF receiving coil may correct the local clock based on the time difference, so as to maintain a constant phase difference between clock signals generated by the local clock generator and the system clock generator. After the local clock generator is corrected, in response to the local clock, the RF receiving coil may acquire MR echo signals by scanning at least a part of the subject. The acquired echo signals may be wirelessly sent, via the signal channel, to the system side assembly for further processing.

In some embodiments, the time difference may also be determined as described in connection with FIGS. 10A and 10B. The acquired MR echo signals and the time information may be wirelessly sent to the system side assembly via the signal channel. The system side assembly may further generate K space data based on the MR echo signals and the time information. The K space data may be further processed to reconstruct an MR image.

As shown in FIG. 13, similar to operations 1301-1304, operations 1305-1308 illustrate the synchronization process between a second RF receiving coil (e.g., RF receiving coil 2) and the system side assembly, and not repeated herein. Merely for illustration, the synchronization processes for only two RF receiving coils are illustrated in FIG. 13. It should be noted that, for the plurality of RF receiving coils, multiple RF receiving coils may perform the synchronization process synchronously or asynchronously.

As described in connection with FIGS. 2A-2B, or FIGS. 11-12. The MRI device may include a coil side assembly (e.g., the coil side assembly 1400 shown in FIG. 14) and a system side assembly (e.g., the system side assembly 1500 shown in FIG. 15). More descriptions of one or more components in the coil side assembly and/or the system side assembly may be found elsewhere in the present disclosure, for example, FIGS. 14-17, and the descriptions thereof.

Figure 14:
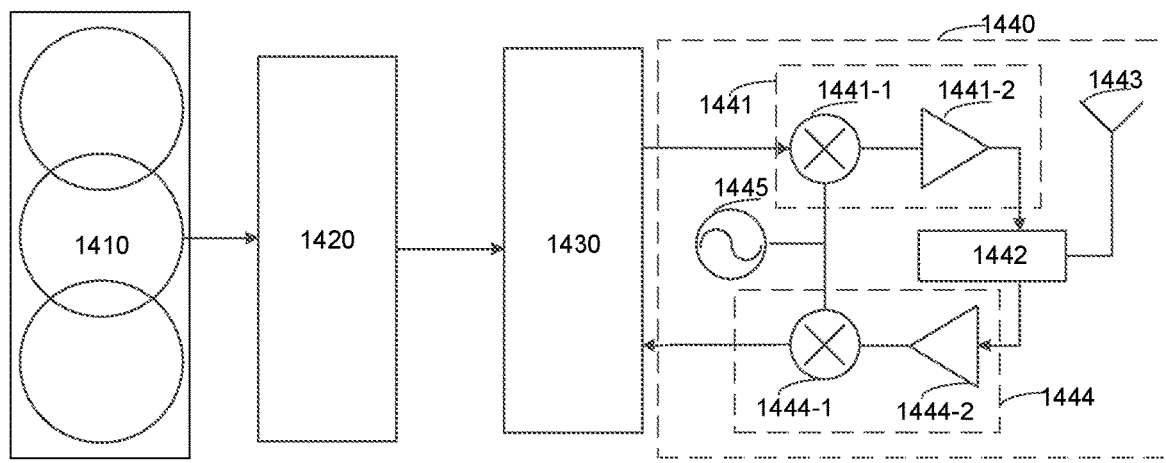
FIG. 14 is a schematic diagram illustrating an exemplary coil side assembly according to some embodiments of the present disclosure.

FIG. 14 is a schematic diagram illustrating an exemplary coil side assembly according to some embodiments of the present disclosure. As shown in FIG. 14, coil side assembly 1400 may include a coil module 1410, an analog-to-digital conversion module 1420, a processor 1430, and a first signal transmitter 1440. In some embodiments, the coil module 1410 may include a plurality of RF receiving coils for detecting or acquiring an MR signal (or an MR echo signal). The RF receiving coil may include a birdcage coil, a solenoid coil, a saddle coil, a Helmholtz coil, a phased array coil, a transverse electro-magnetic coil, a loop coil, or the like, or any combination thereof. In some embodiments, the analog-to-digital conversion module 1420 may be operably connected to the coil module 1410. The analog-to-digital conversion module 1420 may receive the MR signal, and digitize the MR signal by performing analog-to-digital conversion to generate a digital MR signal. In some embodiments, the processor 1430 may be operably coupled to the analog-to-digital conversion module 1420. The processor 1430 may receive the digitized MR signal, and modulate the digitized MR signal with a carrier. The corresponding modulated signal may be generated. The processor 1430 may be configured to control the acquisition or detection of an MR signal in response to one or more control signals from the system side assembly. The processor 1430 may include a processing device for data processing, e.g., a central processing unit (CPU), a digital signal processor (DSP), a system on a chip (SoC), a microcontroller unit (MCU), a field editable gate array, or a single chip microcomputer (SCM). In some embodiments, the first signal transmitter 1440 may be operably connected to the processor 1430. The first signal transmitter 1440 may receive the modulated MR signal from the processor 1430, and wirelessly send the modulated MR signal to the system side assembly (e.g., the system side assembly 1500) via a wireless communication network. The first signal transmitter 1440 may receive the one or more control signals from the system side assembly, and send the one or more control signals to the processor 1430. In some embodiments, the first signal transmitter 1440 may communicate with the processor 14300 via the network, such as 2G network, 3G network, 4G network, 5G network, WIFI, Bluetooth, Near Field Communication (NFC), etc.

Figure 15:
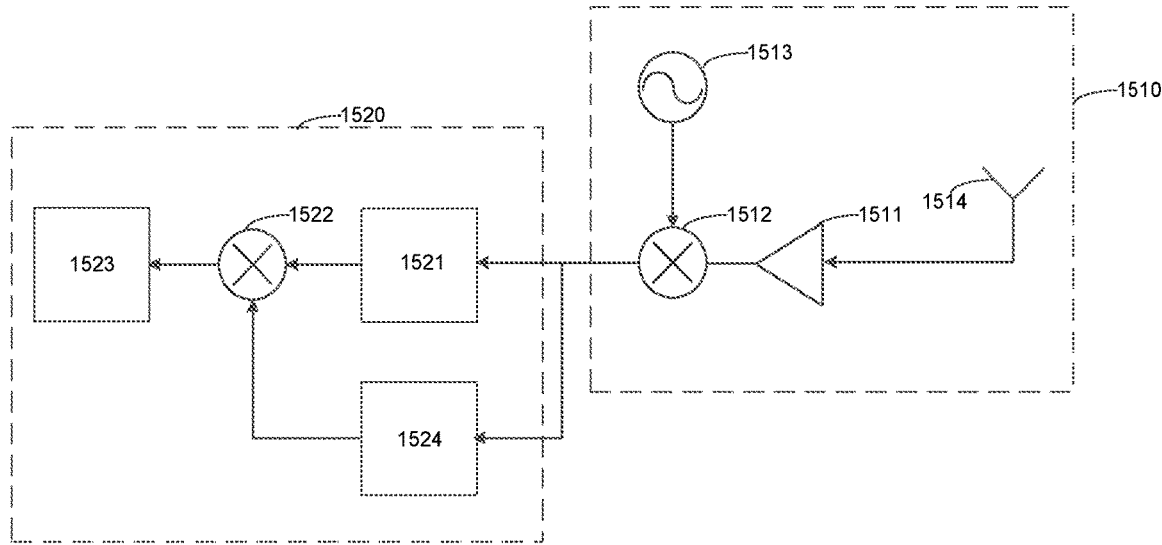
FIG. 15 is a schematic diagram illustrating an exemplary system side assembly according to some embodiments of the present disclosure.

FIG. 15 is a schematic diagram illustrating an exemplary system side assembly according to some embodiments of the present disclosure. As shown in FIG. 15, the system side assembly 1500 may include a second signal transmitter 1510 and a coherent demodulator 1520. The second signal transmitter 1510 may receive the modulated MR signal from the first signal transmitter 1440 at the coil side assembly 1400. The coherent demodulator 1520 may be operably connected to the second signal transmitter 1510. The coherent demodulator 1520 may acquire a carrier signal, and demodulate the modulated MR signal with the carrier signal to recover the MR signal.

As described in connection with FIGS. 14 and 15, the coil module 1410 at the coils side assembly 1400 may acquire MR signals in real time or near time, and transmit the MR signals to an amplifier (not shown in FIG. 14). The amplifier may amplify the MR signals, and improve the signal-to-noise ratio (SNR) of the MR signals. The amplified MR signals may be transmitted to a filter (not shown in FIG. 14). The filter may filter out-of-band signal(s) of the MR signals. The filtered MR signals may be transmitted to the analog-to-digital conversion module 1420. The analog-to-digital conversion module 1420 may perform analog to digital conversion to generate digital MR signals. The processor 1430 may modulate the digital MR signals, and wirelessly transmit the modulated MR signals to the second signal transmitter 1510 at the system side assembly 1500 through the first signal transmitter 1440. The second signal transmitter 1510 may receive the modulated MR signals and perform demodulation operation by using the coherent demodulator 1520 to obtain a recovered digital MR signal. The digital MR signals may be used to reconstruct an MR image.

In some embodiments, as shown in FIG. 15, the coherent demodulator 1520 may include a first band-pass filter 1521, a first mixer 1522, a first low-pass filter 1523, and a carrier recovery unit 1524. The first band-pass filter 1521 may be operably connected to the second signal transmitter 1510. The first band-pass filter 1521 may receive the modulated MR signals, and filter out noises of the modulated MR signals to generate filtered modulated MR signals. The carrier recovery unit 1524 may be operably connected to the second signal transmitter 1510. The carrier recovery unit 1524 may receive the modulated MR signals, and acquire a carrier signal from the modulated MR signals. The first mixer 1522 may connect to the first band-pass filter 1521 and the carrier recovery unit 1524. The first mixer 1522 may receive the filtered modulated MR signals and the carrier signal, and mix the filtered modulated MR signals and the carrier signal. The mixed signals may be generated. The first low-pass filtering 1523 may be operably connected to the first mixer 1522. The first low-pass filtering 1523 may receive the mixed signals, and filter out the high-frequency information of the mixed signal to recover the MR signals.

In some embodiments, the coherent demodulator 1520 may receive the modulated MR signals, then filter out the noises of the modulated MR signals by using the first band-pass filter 1521. The filtered modulated MR signals may be sent to the first mixer 1522. The carrier recovery unit 1524 may receive the modulated MR signals, and recover the carrier signal from the modulated MR signals. The recover carrier signal may be in the same phase with the carrier signal used in the modulation operated by the coil side assembly 1400. The recovered carrier signal may be sent to the first mixer 1522. The first mixer 1522 may mix the filtered modulated signal and the carrier signal to generate the mixed signal. The first low-pass filter 1523 may filter out the high-frequency information of the mixed signal to recover the MR signal. In some embodiments, the carrier recovery unit 1524 may include a squaring loop circuit (e.g., the squaring loop circuit 1600 illustrated in FIG. 16) or a Castas loop circuit (e.g., the Castas loop circuit 1700 illustrated in FIG. 17).

Figure 16:
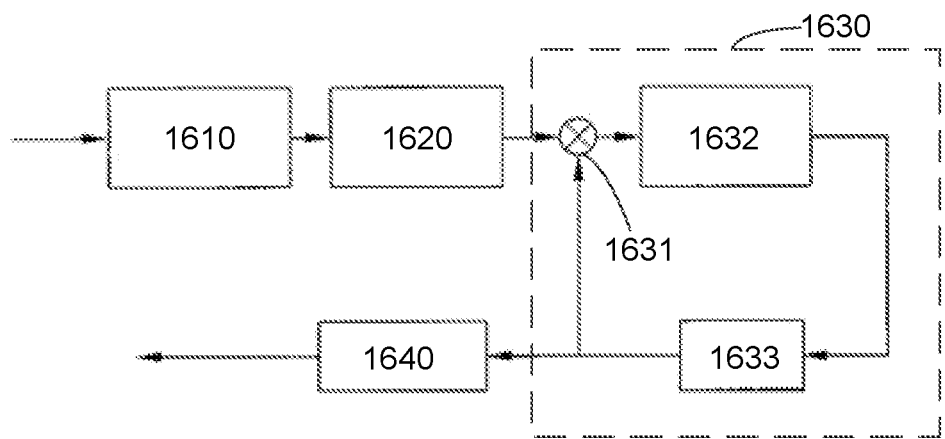
FIG. 16 is a schematic diagram illustrating an exemplary squaring loop circuit according to some embodiments of the present disclosure.

As described in connection with FIG. 16, FIG. 16 illustrates an exemplary squaring loop circuit according to some embodiments of the present disclosure. The square loop circuit 1600 may include a square law unit 1610, a second band-pass filter 1620, a phase-locked loop 1630, and a second frequency divider 1640. The square law unit 1610 may be operably connected to the second signal transmitter 1510. The square law unit 1610 may receive the modulated MR signal, and perform a squaring operation for the modulated MR signal to generate a multi-frequency signal. The second band-pass filter 1620 may be operably coupled to the square law unit 1610. The second band-pass filter 1620 may receive the multi-frequency signal, and filter out the DC (Direct Current) component and the noises of the multi-frequency signal. The phase-locked loop 1630 may be operably connected to the second band-pass filter 1620. The phase-locked loop 1630 may receive the filtered multi-frequency signal, and output a phase-locked signal by performing a phase-locking operation. The second frequency divider 1640 may be operably coupled to the phase-locked loop 1630. The second frequency divider 1640 may receive the phase-locked signal, and perform two-frequency operation for the phase-locked signal to generate the carrier signal. The carrier signal may be sent to the first mixer 1522.

In some embodiments, the square loop circuit 1600 may receive the modulated MR signal, for example, the square law unit 1610 may receive the modulated MR signal from the second signal transmitter 1510. In some embodiments, the modulated MR signal may be expressed by equation (5) as follows:

$$r(t)=s(t)+n(t)=m(t)\sin[\omega_0 t+\theta_1(t)]+n(t), \quad (5)$$

where r(t) denotes the modulated MR signal received by the square law unit, s(t) denotes a raw MR signal, n(t) denotes a noise, m(t) denotes the MR signal before modulating, $\omega_0$ denotes a carrier frequency, and $\theta_1$ denotes a carrier phase. The square law unit 1610 may perform the squaring operation for the modulated MR signal. Then the second band-pass filter 1620 may filter the signal processed by the square law unit 1610. In some embodiments, a center frequency of the second band-pass filter 1620 may be designated as $2f_0$, and a bandwidth of the second band-pass filter 1620 may be designated as $B_t$. The phase locked loop 1630 may process the filtered signal, and output the phase-locked signal, $u_0(t)=U_0 \sin(2\omega_0 t+2\theta_2(t))$. The second frequency divider 1640 may perform two-frequency operation for the phase-locked signal. The second frequency divider 1640 may extract the signal whose frequency is $2\pi f_0$, that is, $\omega_0=2\pi f_0$, and designate the extracted signal as the carrier signal. Where $f_0$ is the center frequency matching with an original carrier frequency, $B_t$ is the bandwidth of the second band-pass filter, $u_0(t)$ denotes an output phase-locked signal, $\omega_0$ denotes a carrier frequency, $\theta_2$ denotes a phase of the carrier. In some embodiments, the phase-locked loop 1630 may include a first phase detector 1631, a first loop filter 1632, and a first voltage controlled oscillator (VCO) 1633. The first phase detector 1631 may be operably connected to the second band-pass filter 1620 and the first voltage controlled oscillator 1633. The first phase detector 1631 may receive the filtered multi-frequency signal and the phase-locked signal, and generate a first phase difference signal between the filtered multi-frequency signal and the phase-locked signal. The first loop filter 1632 may receive the first phase difference signal from the first phase detector 1631, and filter out noises of the first phase difference signal to output a control signal. Then the first voltage controlled oscillator 1633 may receive the control signal, and generate the phase-locked signal in response to the control signal. The phase-locked signal may be sent to the first phase detector 1631 and the second frequency divider 1640.

Figure 17:
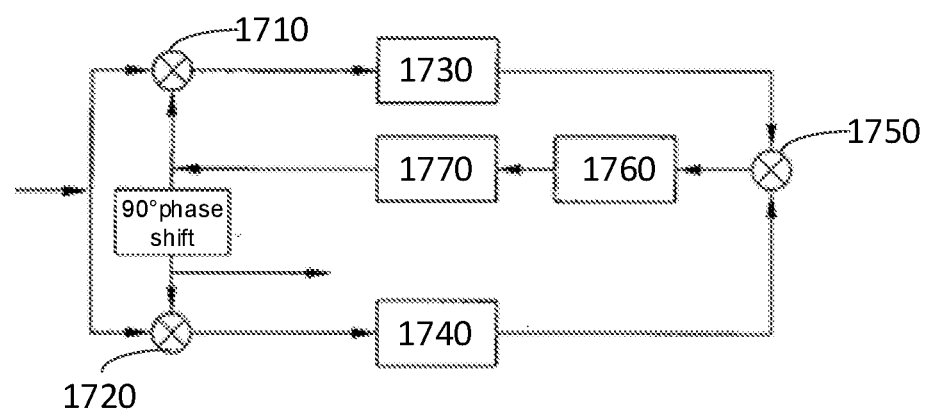
FIG. 17 is a schematic diagram illustrating an exemplary Castas loop circuit according to some embodiments of the present disclosure.

As described in connection with FIG. 17, FIG. 17 illustrates an exemplary Castas loop circuit according to some embodiments of the present disclosure. As shown in FIG. 17, the Castas loop circuit 1700 may include a second phase detector 1710, a third phase detector 1720, a second low-pass filter 1730, a third low-pass filter 1740, a multiplier 1750, a second loop filter 1760, and a second voltage controlled oscillator 1770. The second phase detector 1710 may be operably connected to the second signal transmitter 1510 and the second voltage controlled oscillator 1770. The second phase detector 1710 may receive the modulated MR signal and the carrier signal, and generate a second phase difference signal by processing the modulated signal and the carrier signal. The third phase detector 1720 may be operably connected to the second signal transmitter 1510 and the second voltage controlled oscillator 1770. The third phase detector 1720 may receive the modulated signal and a phase-shifted carrier signal whose phase is shifted by 90 degrees compared to the carrier signal (hereinafter 90° phase-shift carrier signal), and generate a third phase difference signal by processing the modulated signal and the 90° phase-shift carrier signal. The second low-pass filter 1730 may be operably connected to the second phase detector 1710. The second low-pass filter 1730 may receive the second phase difference signal, and perform low pass filtering for the second phase difference signal to output a filtered second phase difference signal. The third low-pass filter 1740 may be operably connected to the third phase detector 1720. The third low-pass filter 1740 may receive the third phase difference signal, and perform low pass filtering for the third phase difference signal to output a filtered third phase difference signal. The multiplier 1750 may operably coupled to the second low-pass filter 1730 and the third low-pass filter 1740. The multiplier 1750 may receive the filtered second phase difference signal and the filtered third phase difference signal, and multiply the filtered second phase difference signal and the filtered third phase difference signal to generate an error signal. The second loop filter 1760 may be connected to the multiplier 1750. The second loop filter 1760 may receive the error signal, and filter out noises of the error signal to generate a second control signal. The second voltage controlled oscillator 1770 may be operably connected to the second loop filter 1760. The second voltage controlled oscillator 1770 may receive the second control signal, and generate the carrier signal and the 90° phase-shift carrier signal in response to the second control signal. The carrier signal may be sent to the second phase detector 1710 and the first mixer 1522. The 90° phase-shift carrier signal may be sent to the third phase detector 1720.

Specifically, the Castas loop may be configured to output the coherent carrier. The Castas loop circuit may receive the modulated MR signal, that is, the second phase detector 1710 and the third phase detector 1720 receive the modulated MR signal. The modulated signal may be expressed by equation (6) as follows:

$$r(t)=s(t)+n(t)=m(t)\sin[\omega_0 t+\theta_1(t)]+n(t) \quad (6)$$

where r(t) denotes the modulated MR signal received by the square law unit, s(t) denotes a raw MR signal, n(t) denotes a noise, m(t) denotes the MR signal before modulating, $\omega_0$ denotes a carrier frequency, and $\theta_1$ denotes a carrier phase. The second phase detector 1710 may generate the second phase difference signal by processing the modulated signal and the carrier signal. The third phase detector 1720 may generate the third phase difference signal by processing the modulated signal and 90° phase-shifted carrier signal. The second low pass filter 1730 may filter the second phase difference signal, and output a filtered second phase difference signal. The third low pass filter 1740 may filter the third phase difference signal, and output a filtered third phase difference signal. The filtered second phase difference signal and the filtered third phase difference signal may be multiplied by the multiplier 1750. Then the multiplier 1750 may output the error signal. The error signal may pass through the second loop filter 1760 and the second voltage controlled oscillator 1770. The second voltage controlled oscillator 1770 may output the carrier signal for coherent demodulation.

In some embodiments, as described in connection with FIG. 14, the first signal transmitter 1440 may include a first oscillator 1445, a transmitting unit 1441, a duplexer 1442, a first antenna 1443, and a receiving unit 1444. The transmitting unit 1441 may be operably connected to the processor 1430. The transmitting unit 1441 may receive the modulated MR signal, and mix the modulated MR signal with a local oscillator signal. The mixed signal may be amplified, then transmitted to a duplexer 1442. The duplexer 1442 may be operably connected to the transmitting unit 1441. The duplexer 1442 may send the received signal to a first antenna 1443. In some embodiments, the duplexer 1442 may be further configured to receive the MR control signal, and transmit the MR control signal to a receiving unit 1444. The first antenna 1443 may be operably connected to the duplexer 1442. The first antenna 1443 may receive the modulated MR signal after mixing and amplifying, and wirelessly send the received signal to the system side assembly 1500. The first antenna 1443 may receive an MR control signal sent by the system side assembly 1500, and transmit the MR control signal to the duplexer 1442. The receiving unit 1444 may be operably coupled to the duplexer 1442. The receiving unit 1444 may receive the MR control signal. The receiving unit 1444 may amplify the signal, and mix the amplified signal with the local oscillator signal. The receiving unit 1444 may send the mixed signal to the processor 1430. The first oscillator 1445 may be operably connected to the transmitting unit 1441 and the receiving unit 1444. The first oscillator 1445 may provide the local oscillator signal for the transmitting unit 1441 and the receiving unit 1444. The processor 1430 may receive the MR control signal sent by a second signal transmitter 1510 of the system side assembly 1500 through the first antenna 1443. The first antenna 1443 may transmit the MR control signal to the processor 1430 of the coil side assembly 1400 through the first signal transmitter 1440. The coil side assembly 1400 may remain synchronized with the system side assembly 1500 in response to the MR control signal.

Specifically, the transmitting unit 1441 may mix the modulated MR signal with the local oscillator signal. The transmitting unit 1441 may amplify the mixed signal, and transmit the amplified signal to the duplexer 1442. In some embodiments, the duplexer 1442 may isolate the transmitted and received signals. The duplexer 1442 may transmit the modulated MR signal with the mixing and amplifying to the first antenna 1443. The first antenna 1443 may transmit the received signal to the system side assembly 1500. In some embodiments, the first antenna 1443 may also receive the MR control signal, and transmit the MR control signal to the receiving unit 1444 through the duplexer 1442. The receiving unit 1444 may amplify the MR control signal, and mix the amplified signal with the local oscillator signal. The mixed signal may be sent to the processor 1430. In some embodiments, the transmitting unit 1441 may include a second mixer 1441-1 and a power amplifier 1441-2. The second mixer 1441-1 may be operably connected to the processor 1430. The second mixer 1441-1 may receive a modulated MR signal, and mix the modulated MR signal with the local oscillator signal. The mixed signal may be sent to the power amplifier 1441-2. The power amplifier 1441-2 may amplify the mixed modulated MR signal. The amplified signal may be transmitted to the duplexer 1442. In some embodiments, the receiving unit 1444 may include a third mixer 1444-1 and a first preamplifier 1444-2. The first preamplifier 1444-2 may be operably connected to the duplexer 1442. The first preamplifier 1444-2 may receive the MR control signal, and amplify the MR control signal. The third mixer 1444-1 may be operably connected to the first preamplifier 1444-2. The third mixer 1444-1 may receive the amplified MR control signal, and mix the amplified MR control signal with the local oscillator signal. After the mixing, the mixed signal may be transmitted to the processor 1430.

In some embodiments, as described in connection with FIG. 15, the second signal transmitter 1510 may include a second preamplifier 1511, a fourth mixer 1512, a second oscillator 1513, and a second antenna 1514. The second oscillator 1513 may be operably connected to the fourth mixer 1512. The second oscillator 1513 may provide a local oscillator signal for the fourth mixer 1512. The second antenna 1514 may receive the modulated MR signal sent by the coil side assembly 1400. The second preamplifier 1511 may be operably connected to the second antenna 1510. The second preamplifier 1511 may receive the modulated MR signal and amplify the modulated MR signal. The fourth mixer 1512 may be operably connected to the second preamplifier 1511. The fourth mixer 1512 may receive the amplified modulated MR signal, and mixed the received signal with the localized signal. The mixed signal may be transmitted to the coherent demodulator 1520.

In some embodiments, the second antenna 1514 may receive the modulated MR signal sent by the coil side assembly 1400. The preamplifier 1511 may amplify the modulated signal. Then the fourth mixer 1512 may mix the amplified signal with the local oscillator signal. The mixed signal may be transmitted to the coherent demodulator 1520. The second oscillator 1513 may provide the local oscillator signal for the fourth mixer 1512.

The MRI device may include a coil side assembly and a system side assembly. The coil side assembly may include a coil module, an analog-to-digital conversion module, a processor and a first signal transmitter. The coil module may be configured to acquire an MR signal. The analog-to-digital conversion module, which is operably coupled to the coil module, may receive the MR signal, and perform analog to digital conversion for the MR signal to obtain a digital MR signal. The processor, which is operably coupled to the analog-to-digital conversion module, may receive the digital MR signal and modulate the digital MR signal. The first signal transmitter, which is operably connected to the processor, may receive the modulated MR signal, and wirelessly transmit the modulated signal to the system side assembly. The system side assembly may wirelessly communicate with the coil side assembly. The system side assembly may parse the digital MR signal from the modulated signal. In some embodiments, the coil side assembly may include a phased array coil, and the phased array coil is synchronized with the system side assembly.

In some embodiments, the coil module may include a birdcage coil, a solenoid coil, a saddle coil, a Helmholtz coil, a phased array coil, a transverse electro-magnetic coil, a loop coil, or the like, or any combination thereof. For example, the coil module 1410 may be the phased array coil.

The MRI device may acquire the MR signal by a coil module at a coil side assembly. The MRI device may convert the analog MR signal into the digital MR signal through an analog-to-digital conversion module. The digital MR signal may be modulated by the processor. The modulated MR signal may be sent to the system side assembly through the first signal transmitter. The second signal transmitter at the system side assembly may receive the modulated MR signal, and transmit the modulated MR signal to the coherent demodulator. The coherent demodulator may demodulate the modulated MR signal to recover the digital MR signal, which may be used for image reconstruction. The first signal transmitter at the coil side assembly may be further configured to receive the MR control signal and transmit the MR control signal to the processor. The processor may control the acquisition of the MR signal in response to the MR control signal. The wireless transmission may reduce the cost of using conventional RF wires or optical fibers to connect the coil side assembly and the system side assembly, and improve convenience of scanning operation.

It should be noted that the connection between different modules or functional components in the present disclosure may be realized through a wireless connection. For example, the connection between the first signal transmitter 1440 and the processor 1430, the connection between the analog-to-digital conversion module 1420 and the coil module 1410, the connection between the processor 1430 and the analog-to-digital conversion module 1420, or the first signal transmitter 1440 and the second signal transmitter 1510 at the system side assembly 1500. The signal wireless transmission may include radio waves wireless communication, infrared rays communication, etc. Different network types, such as a wireless local area network (WLAN), a wireless personal area network (WPAN), or a low-speed wireless personal area network (LR-WPAN), may be formed between different modules and units.

Some embodiments of the present invention can also be embodied as follows:

Embodiment 1: An imaging system implemented on a magnetic resonance imaging (MRI) device including a coil side assembly and a system side assembly, comprising:

a storage device including a set of instructions;

at least one processor in communication with the storage device, wherein when executing the set of instructions, the at least one processor is configured to direct the system to:

acquire, at the coil side assembly, magnetic resonance (MR) echo signals;

record, at the coil side assembly, time information regarding the MR echo signals, wherein the time information includes acquisition time of each echo signal, and a time difference regarding a local clock generator at the coil side assembly and a system clock generator at the system side assembly;

wirelessly send, via a signal transmitter system, the MR echo signals and the time information from the coil side assembly to the system side assembly;

generat K space data, at the system coil assembly, based on the time information and the MR echo signals; and reconstruct, at the system side assembly, an MR image based on the K space data.

Embodiment 2: A method for magnetic resonance (MR) signal synchronization between a coil side assembly and a system side assembly of a magnetic resonance imaging (MRI) device, comprising:

for each of a plurality of radio frequency (RF) receiving coils disposed in the coil side assembly, sending, via a signal transmitter system, wirelessly a request for communicating with the system side assembly to the system side assembly, the request including a first timestamp recording when the request is sent by the RF receiving coil;

receiving, via the signal transmitter system, wirelessly a permission from the system side assembly to communicate with the system side assembly, the permission including the first timestamp, a second timestamp recording when the request is received by the system side assembly, a third timestamp recording when the response is sent by the system side assembly;

registering a fourth timestamp recording when the permission is received by the RF receiving coil;

determining a time difference in the RF receiving coil compared to the system side assembly based on the first timestamp, the second timestamp, the third timestamp, and the fourth timestamp; and maintaining a constant phase difference between clock signals generated by the local clock generator and a system clock generator by correcting, based on the time difference, a local clock generator of the RF receiving coil.

Embodiment 3: The method of embodiment 2, wherein the request further includes a coil characteristic of the RF receiving coil, the method further comprising:

in response to the request, assigning, at the system side assembly and based on the coil characteristic, a signal channel for communication between the RF receiving coil and the system side assembly; and sending, via the signal channel, the permission to the coil side assembly.

Embodiment 4: The method of embodiment 3, wherein the assigning, at the system side assembly and based on the coil characteristic, a signal channel for communication between the RF receiving coil and the system side assembly further includes:

assigning the signal channel for the RF receiving coil using a Frequency Division Multiple Access (FDMA) technique or a Code Division Multiple Access (CDMA) technique.

Embodiment 5: A magnetic resonance imaging (MRI) device including a coil side assembly and a system side assembly, wherein:

the coil side assembly further includes:
  a coil module for detecting an MR signal, the coil module including a plurality of radio frequency (RF) receiving coils;
  an analog-to-digital conversion module for digitizing the MR signal;
  a processor for receiving the digitized MR signal and modulating the digitized MR signal; and
  a first signal transmitter for wirelessly sending the modulated MR signal to a second signal transmitter of the system side assembly;
the system side assembly further includes:
  the second signal transmitter for receiving the modulated MR signal from the first signal transmitter; and
  a coherent demodulator for acquiring a carrier signal from the modulated MR signal and demodulating, based on the carrier signal, the modulated MR signal to recover the MR signal.

Embodiment 6: The device of embodiment 5, wherein the coherent demodulator further includes:
  a first band-pass filter for filtering the modulated MR signal;
  a carrier recovery unit for acquiring the carrier signal from the modulated MR signal;
  a first mixer for mixing the filtered MR signal and the carrier signal to generate a mixed signal; and
  a first low-pass filter for filtering out high-frequency information of the mixed signal to recover the MR signal.

Embodiment 7: The device of embodiment 6, wherein the carrier recovery unit further includes a squaring loop circuit, wherein the squaring loop circuit further includes:
  a square law unit for generating a multi-frequency signal by processing the modulated MR signal;
  a second band-pass filter for filtering the multi-frequency signal;
  a phase-locked loop for outputting a phase-locked signal by performing a phase-locking operation for the filtered multi-frequency signal; and
  a frequency divider for generating the carrier signal by processing the phase-locked signal.

Embodiment 8: The device of embodiment 7, wherein the phase-locked loop further includes:
  a first phase detector for generating a first phase difference signal by processing the filtered multi-frequency signal and the phase-locked signal;
  a first loop filter for filtering the first phase difference signal to output a control signal; and
  a first voltage controlled oscillator for generating the phase-locked signal in response to the control signal, and sending the phase-locked signal to the first phase detector and the frequency divider.

Embodiment 9: The device of embodiment 6, wherein the carrier recovery unit further includes a Castas loop circuit, wherein the Castas loop circuit further includes:
  a second phase detector for generating a second phase difference signal by processing the modulated signal and the carrier signal;
  a third phase detector for generating a third phase difference signal by processing the modulated signal and a phase-shifted carrier signal whose phase is shifted by 90 degrees compared to the carrier signal;
  a second low-pass filter for filtering the second phase difference signal;
  a third low-pass filter for filtering the third phase difference signal;
  a multiplier for generating an error signal by processing the filtered second phase difference signal and the filtered third phase difference signal;
  a second loop filter for filtering the error signal to output a second control signal; and
  a second voltage controlled oscillator for generating the carrier signal and the phase-shifted carrier signal in response to the second control signal.

Embodiment 10: The device of embodiment 5, wherein the first signal transmitter further includes:
  a transmitting unit including a second mixer for mixing the modulated MR signal with a local oscillator signal, a power amplifier for amplifying the mixed signal and transmitting the amplified signal to a duplexer;
  the duplexer for transmitting the received MR signal to an antenna;
  the antenna for wirelessly transmitting the MR signal to the second signal transmitter of the system side assembly;
  a receiving unit including a first preamplifier for receiving an MR control signal from the system side assembly and amplifying the MR control signal, a third mixer for mixing the amplified MR control signal with the local oscillator signal and transmitting the amplified signal to the processor; and
  an oscillator for providing the local oscillator signal for the transmitting unit and the receiving unit.

Embodiment 11: The device of embodiment 5, wherein the second signal transmitter further includes:
  a second oscillator for providing a second local oscillator signal for a fourth mixer;
  a second antenna for receiving the modulated MR signal from the antenna of the coil side assembly;
  a second preamplifier for amplifying the modulated MR signal; and
  the fourth mixer for mixing the amplified modulated MR signal with the second local oscillator signal to transmit to the coherent demodulator.

Having thus described the basic concepts, it may be rather apparent to those skilled in the art after reading this detailed disclosure that the foregoing detailed disclosure is intended to be presented by way of example only and is not limiting. Various alterations, improvements, and modifications may occur and are intended to those skilled in the art, though not expressly stated herein. These alterations, improvements, and modifications are intended to be suggested by the present disclosure, and are within the spirit and scope of the exemplary embodiments of the present disclosure.

Moreover, certain terminology has been used to describe embodiments of the present disclosure. For example, the terms "one embodiment," "an embodiment," and/or "some embodiments" mean that a particular feature, structure or characteristic described in connection with the embodiment is included in at least one embodiment of the present disclosure. Therefore, it is emphasized and should be appreciated that two or more references to "an embodiment" or "one embodiment" or "an alternative embodiment" in various portions of this specification are not necessarily all referring to the same embodiment. Furthermore, the particular features, structures or characteristics may be combined as suitable in one or more embodiments of the present disclosure.

Further, it will be appreciated by one skilled in the art, aspects of the present disclosure may be illustrated and described herein in any of a number of patentable classes or context including any new and useful process, machine, manufacture, or composition of matter, or any new and useful improvement thereof. Accordingly, aspects of the present disclosure may be implemented entirely hardware, entirely software (including firmware, resident software, micro-code, etc.) or combining software and hardware implementation that may all generally be referred to herein as a "unit," "module," or "system." Furthermore, aspects of the present disclosure may take the form of a computer program product embodied in one or more computer readable media having computer readable program code embodied thereon.

A computer readable signal medium may include a propagated data signal with computer readable program code embodied therein, for example, in baseband or as part of a carrier wave. Such a propagated signal may take any of a variety of forms, including electro-magnetic, optical, or the like, or any suitable combination thereof. A computer readable signal medium may be any computer readable medium that is not a computer readable storage medium and that may communicate, propagate, or transport a program for use by or in connection with an instruction execution system, apparatus, or device. Program code embodied on a computer readable signal medium may be transmitted using any appropriate medium, including wireless, wireline, optical fiber cable, radio frequency (RF), or the like, or any suitable combination of the foregoing.

Computer program code for carrying out operations for aspects of the present disclosure may be written in any combination of one or more programming languages, including an object oriented programming language such as Java, Scala, Smalltalk, Eiffel, JADE, Emerald, C++, C#, VB. NET, Python or the like, conventional procedural programming languages, such as the "C" programming language, Visual Basic, Fortran 2103, Perl, COBOL 2102, PHP, ABAP, dynamic programming languages such as Python, Ruby and Groovy, or other programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider) or in a cloud computing environment or offered as a service such as a Software as a Service (SaaS).

Furthermore, the recited order of processing elements or sequences, or the use of numbers, letters, or other designations, therefore, is not intended to limit the claimed processes and methods to any order except as may be specified in the claims. Although the above disclosure discusses through various examples what is currently considered to be a variety of useful embodiments of the disclosure, it is to be understood that such detail is solely for that purpose and that the appended claims are not limited to the disclosed embodiments, but, on the contrary, are intended to surface modifications and equivalent arrangements that are within the spirit and scope of the disclosed embodiments. For example, although the implementation of various components described above may be embodied in a hardware device, it may also be implemented as a software only solution, for example, an installation on an existing server or mobile device.

Similarly, it should be appreciated that in the foregoing description of embodiments of the present disclosure, various features are sometimes grouped in a single embodiment, figure, or description thereof for the purpose of streamlining the disclosure aiding in the understanding of one or more of the various inventive embodiments. This method of disclosure, however, is not to be interpreted as reflecting an intention that the claimed subject matter requires more features than are expressly recited in each claim. Rather, inventive embodiments lie in less than all features of a single foregoing disclosed embodiment.

In some embodiments, the numbers expressing quantities or properties used to describe and claim certain embodiments of the application are to be understood as being modified in some instances by the term "about," "approximate," or "substantially." For example, "about," "approximate," or "substantially" may indicate ±20% variation of the value it describes, unless otherwise stated. Accordingly, in some embodiments, the numerical parameters set forth in the written description and attached claims are approximations that may vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the application are approximations, the numerical values set forth in the specific examples are reported as precisely as practicable.

Each of the patents, patent applications, publications of patent applications, and other material, such as articles, books, specifications, publications, documents, things, and/or the like, referenced herein is hereby incorporated herein by this reference in its entirety for all purposes, excepting any prosecution file history associated with same, any of same that is inconsistent with or in conflict with the present document, or any of same that may have a limiting affect as to the broadest scope of the claims now or later associated with the present document. By way of example, should there be any inconsistency or conflict between the description, definition, and/or the use of a term associated with any of the incorporated material and that associated with the present document, the description, definition, and/or the use of the term in the present document shall prevail.

In closing, it is to be understood that the embodiments of the application disclosed herein are illustrative of the principles of the embodiments of the application. Other modifications that may be employed may be within the scope of the application. Thus, by way of example, but not of limitation, alternative configurations of the embodiments of the application may be utilized in accordance with the teachings herein. Accordingly, embodiments of the present application are not limited to that precisely as shown and described.

What is claimed is:

1. A method for magnetic resonance (MR) signal synchronization between a coil side assembly and a system side assembly of a magnetic resonance imaging (MRI) device, comprising:
   determining a time difference in a local clock generator at the coil side assembly compared to a system clock generator at the system side assembly;
   maintaining a constant phase difference between clock signals generated by the local clock generator and by the system clock generator by correcting the local clock generator based on the time difference;
   acquiring an MR echo signal by scanning at least a part of a subject in response to the clock signal generated by the corrected local clock generator; and
   digitizing the MR echo signal at the coil side assembly, wherein the determining a time difference in a local clock generator at the coil side assembly compared to a system clock generator at the system side assembly further includes:

determining a time delay in the local clock generator compared to the system clock generator; and determining the time difference based on the time delay, wherein the determining a time delay in the local clock generator compared to the system clock generator further includes:

sending, at the coil side assembly, a first Sync message to the system side assembly, the first Sync message including a first timestamp recording when the first Sync message is sent by the coil side assembly;

receiving, at the coil side assembly, a second Sync message from the system side assembly, and registering a fourth timestamp recording when the second Sync message is received by the coil side assembly, the second Sync message including the first timestamp, a second timestamp recording when the first Sync message is received by the system side assembly, and a third timestamp recording when the second Sync message is sent by the system side assembly; and determining the time delay based on the first timestamp, the second timestamp, the third timestamp, and the fourth timestamp.

2. The method of claim 1, further comprising:
wirelessly sending, via a signal transmitter system, the digitized MR echo signal from the coil side assembly to the system side assembly.

3. The method of claim 1, wherein the digitizing the MR signal at the coil side assembly further includes:
amplifying the MR echo signal;
filtering the amplified MR echo signal; and
digitizing the filtered MR echo signal by performing analog to digital signal conversion.

4. The method of claim 1, further comprising:
wirelessly sending, via a signal transmitter system, the MR echo signal from the coil side assembly to the system side assembly;
generating a K space dataset, at the system side assembly, based on the MR echo signal; and
reconstructing, at the system coil assembly, an MR image based on the K space dataset.

5. The method of claim 1, wherein the coil side assembly comprises a plurality of radio frequency (RF) receiving coils, and wherein for each of the plurality of radio frequency (RF) receiving coils, the determining a time difference in a local clock generator at the coil side assembly compared to a system clock generator at the system side assembly further includes:

sending, via a signal transmitter system, wirelessly a request for communicating with the system side assembly to the system side assembly, the request including the first timestamp recording when the request is sent by the RF receiving coil;

receiving, via the signal transmitter system, wirelessly a permission from the system side assembly to communicate with the system side assembly, the permission including the first timestamp, the second timestamp recording when the request is received by the system side assembly, the third timestamp recording when the response is sent by the system side assembly;

registering the fourth timestamp recording when the permission is received by the RF receiving coil; and determining the time difference in the RF receiving coil compared to the system side assembly based on the first timestamp, the second timestamp, the third timestamp, and the fourth timestamp.

6. The method of claim 5, wherein the request further includes a coil characteristic of the RF receiving coil, the method further comprising:

in response to the request, assigning, at the system side assembly and based on the coil characteristic, a signal channel for communication between the RF receiving coil and the system side assembly; and sending, via the signal channel, the permission to the coil side assembly.

7. The method of claim 6, wherein the assigning, at the system side assembly and based on the coil characteristic, a signal channel for communication between the RF receiving coil and the system side assembly further includes:

assigning the signal channel for the RF receiving coil using a Frequency Division Multiple Access (FDMA) technique or a Code Division Multiple Access (CDMA) technique.

8. A system for magnetic resonance (MR) signal synchronization between a coil side assembly and a system side assembly of a magnetic resonance imaging (MRI) device, comprising:

a storage device including a set of instructions;

at least one processor in communication with the storage device, wherein when executing the set of instructions, the at least one processor is configured to direct the system to:

determine a time difference in a local clock generator at the coil side assembly compared to a system clock generator at the system side assembly;

maintain a constant phase difference between clock signals generated by the local clock generator and by the system clock generator by correcting the local clock generator based on the time difference;

acquire an MR echo signal by scanning at least a part of a subject in response to the clock signal generated by the corrected local clock generator; and digitize the MR echo signal at the coil side assembly, wherein to determine a time difference in a local clock generator at the coil side assembly compared to a system clock generator at the system side assembly, the at least one processor is further configured to direct the system to:

determine a time delay in the local clock generator compared to the system clock generator; and determine the time difference based on the time delay, wherein to determine a time delay in the local clock generator compared to the system clock generator, the at least one processor is further configured to direct the system to:

send, at the coil side assembly, a first Sync message to the system side assembly, the first Sync message including a first timestamp recording when the first Sync message is sent by the coil side assembly;

receive, at the coil side assembly, a second Sync message from the system side assembly, and register a fourth timestamp recording when the second Sync message is received by the coil side assembly, the second Sync message including the first timestamp, a second timestamp recording when the first Sync message is received by the system side assembly, and a third timestamp recording when the second Sync message is sent by the system side assembly; and determine the time delay based on the first timestamp, the second timestamp, the third timestamp, and the fourth timestamp.

9. The system of claim 8, wherein the at least one processor is further configured to direct the system to:
wirelessly send, via a signal transmitter system, the digitized MR echo signal from the coil side assembly to the system side assembly.

10. The system of claim 8, wherein to digitize the MR echo signal at the coil side assembly, the at least one processor is further configured to direct the system to:
amplify the MR echo signal;
filter the amplified MR echo signal; and
digitize the filtered MR echo signal by performing analog to digital signal conversion.

11. The system of claim 8, the at least one processor is further configured to direct the system to:
wirelessly send, via a signal transmitter system, the MR echo signal from the coil side assembly to the system side assembly;
generate a K space dataset, at the system side assembly, based on the MR echo-signal; and
reconstruct, at the system coil assembly, an MR image based on the K space dataset.

12. The system of claim 8, wherein the coil side assembly comprises a plurality of radio frequency (RF) receiving coils, and wherein for each of a plurality of radio frequency (RF) receiving wherein coils, to determine a time difference in a local clock generator at the coil side assembly compared to a system clock generator at the system side assembly, the at least one processor is further configured to direct the system to:
send, via a signal transmitter system, wirelessly a request for communicating with the system side assembly to the system side assembly, the request including the first timestamp recording when the request is sent by the RF receiving coil;
receive, via the signal transmitter system, wirelessly a permission from the system side assembly to communicate with the system side assembly, the permission including the first timestamp, the second timestamp recording when the request is received by the system side assembly, the third timestamp recording when the response is sent by the system side assembly;
register the fourth timestamp recording when the permission is received by the RF receiving coil; and
determine the time difference in the RF receiving coil compared to the system side assembly based on the first timestamp, the second timestamp, the third timestamp, and the fourth timestamp.

13. The method of claim 12, wherein the request further includes a coil characteristic of the RF receiving coil, the at least one processor is further configured to direct the system to:
in response to the request, assign, at the system side assembly and based on the coil characteristic, a signal channel for communication between the RF receiving coil and the system side assembly; and
send, via the signal channel, the permission to the coil side assembly.

14. A system for magnetic resonance (MR) signal synchronization between a coil side assembly and a system side assembly of a magnetic resonance imaging (MRI) device, comprising:
a storage device including a set of instructions;
at least one processor in communication with the storage device, wherein when executing the set of instructions, the at least one processor is configured to direct the system to:
for each of a plurality of radio frequency (RF) receiving coils disposed in the coil side assembly,
send, via a signal transmitter system, wirelessly a request for communicating with the system side assembly to the system side assembly, the request including a first timestamp recording when the request is sent by the RF receiving coil;
receive, via the signal transmitter system, wirelessly a permission from the system side assembly to communicate with the system side assembly, the permission including the first timestamp, a second timestamp recording when the request is received by the system side assembly, a third timestamp recording when the response is sent by the system side assembly;
register a fourth timestamp recording when the permission is received by the RF receiving coil;
determine a time difference in the RF receiving coil compared to the system side assembly based on the first timestamp, the second timestamp, the third timestamp, and the fourth timestamp; and
maintain a constant phase difference between clock signals generated by the local clock generator and a system clock generator by correcting, based on the time difference, a local clock generator of the RF receiving coil.

* * * * *